US011883405B2

(12) United States Patent
Mascha Mensonides-Harsema et al.

(10) Patent No.: US 11,883,405 B2
(45) Date of Patent: Jan. 30, 2024

(54) PHARMACEUTICAL COMPOSITION COMPRISING A COMBINATION OF METHOTREXATE AND NOVOBIOCIN, AND THE USE OF SAID COMPOSITION IN THERAPY

(71) Applicant: Amplio Pharma AB, Lund (SE)

(72) Inventors: Marguérite Mascha Mensonides-Harsema, Houston, TX (US); Charlott Brunmark, Flyinge (SE); Karin von Wachenfeldt, Lund (SE)

(73) Assignee: AMPLIO PHARMA AB, Lund (SE)

( * ) Notice: Subject to any disclaimer, the term of this patent is extended or adjusted under 35 U.S.C. 154(b) by 0 days.

(21) Appl. No.: 16/617,763

(22) PCT Filed: May 31, 2018

(86) PCT No.: PCT/EP2018/064322
§ 371 (c)(1),
(2) Date: Nov. 27, 2019

(87) PCT Pub. No.: WO2018/220101
PCT Pub. Date: Dec. 6, 2018

(65) Prior Publication Data
US 2020/0101074 A1 Apr. 2, 2020

(30) Foreign Application Priority Data
May 31, 2017 (SE) .................... 1750688-2

(51) Int. Cl.
| A61K 31/529 | (2006.01) |
| A61K 9/00 | (2006.01) |
| A61K 9/20 | (2006.01) |
| A61K 31/7048 | (2006.01) |
| A61P 19/02 | (2006.01) |
| A61K 31/519 | (2006.01) |

(52) U.S. Cl.
CPC .......... *A61K 31/519* (2013.01); *A61K 9/0053* (2013.01); *A61K 9/0095* (2013.01); *A61K 9/20* (2013.01); *A61K 31/7048* (2013.01); *A61P 19/02* (2018.01)

(58) Field of Classification Search
CPC ................ A61K 31/519; A61K 9/0053; A61K 31/7048; A61K 9/20; A61K 9/0095; A61P 19/02
USPC .......................................... 514/28
See application file for complete search history.

(56) References Cited

U.S. PATENT DOCUMENTS

2008/0268045 A1* 10/2008 Dervieux ............... A61P 35/00
424/468
2012/0220518 A1* 8/2012 von Recum ......... A61K 9/0024
514/2.3

FOREIGN PATENT DOCUMENTS

| WO | 199722596 A1 | 6/1997 |
| WO | 199732856 A1 | 9/1997 |
| WO | 199730035 A1 | 10/1997 |
| WO | 199813354 A1 | 4/1998 |
| WO | 199902166 A1 | 1/1999 |
| WO | 2000001389 A1 | 1/2000 |
| WO | 200040529 A1 | 7/2000 |
| WO | 200041669 A2 | 7/2000 |
| WO | 2001044239 A2 | 6/2001 |
| WO | 2001064214 A2 | 9/2001 |
| WO | 200192224 A1 | 12/2001 |
| WO | 200204434 A1 | 1/2002 |
| WO | 200208213 A1 | 1/2002 |

OTHER PUBLICATIONS

Hospira, Oct. 2011.*
Takemura et al. (Metabolism, vol. 15, Issue 6, Jun. 1966, pp. 566-576) (abstract sent).*
Mercadante (Cancer Treatment Reviews 2001; 27: 51-61).*
International Search Report dated Aug. 13, 2018 in International Patent Application No. PCT/EP2018/064322.
International Preliminary Report on Patentability dated Sep. 1, 2019 in International Patent Application No. PCT/EP2018/064322.
Written Opinion of the International Searching Authority dated Aug. 13, 2018 in International Patent Application No. PCT/EP2018/064322.
Burt, et al., "Studies of Excised Gray and White Calf Brain", Comp. Biochem. Physiol., 1989, pp. 679-685, vol. 94B, issue 4.
Donnely, et al., "Novobiocin and Additional Inhibitors of the Hsp90 C-Terminal Nucleotide-binding Pocket", Curr. Med. Chem., 2008, pp. 2702-2717, vol. 15, issue 26.
Holden, et al., "Antifolates can potentiate topisomerase II inhibitors in virtro and in vivo", Cancer Chemother. Pharmacol., 1995, pp. 165-171, vol. 36.
Jackson, et al., "Topoisomerase inhibitors as anti-arthritic agents," Inflammation Research, 2008, pp. 126-134, vol. 57.
Malaviya, "Low-Dose Methotrexate (LD-MTX) in Rheumatology Practice—A Most Widely Misunderstood Drug", Current Rheumatology Reviews, 2016, pp. 128-176, issue 12.

(Continued)

*Primary Examiner* — Ganapathy Krishnan
(74) *Attorney, Agent, or Firm* — Viksnins Harris Padys Malen LLP

(57) ABSTRACT

The present invention relates to a pharmaceutical product comprising a combination of methotrexate and novobiocin, or any pharmaceutically acceptable salts of said compounds, and a pharmaceutical composition comprising (i) a therapeutic amount of methotrexate or any pharmaceutically acceptable salts thereof, and one or more pharmaceutically acceptable excipient, carrier or diluent, (ii) a non-therapeutic amount of novobiocin or any pharmaceutically acceptable salts thereof, and one or more pharmaceutically acceptable excipient, carrier or diluent. The invention further relates to a use of the pharmaceutical product and composition in therapy, such as prevention, progression prophylaxis and/or treatment of autoimmune diseases.

17 Claims, No Drawings

(56) References Cited

OTHER PUBLICATIONS

Martel-Pelletier, et al., "Are Cytokines Involved in Osteoarthritic Pathophysiology?", Seminars in Arthritis and Rheumatism, 1991, pp. 12-25, vol. 20, issue 6.

Nose, et al., "Neuromuscular target recognition by a homophilic interaction of Connection cell adhesion molecules in *Drosophila*," Development, 1997, pp. 1433-1441, vol. 124.

Oteo, et al., "Increase of resistance to macrolides in invasice *Streptococcus pneumoniae* in Spain", Clinical Microbiology and Infection, 2005, p. 851-854, vol. 10, issue 9.

Gras et al., "Stucture of the calcium pyrophosphate monohydrate phase: towards understanding the dehydration process in calcium pyrophosphate hydrates," Structural Chemistry, 2014, pp. 862-866.

Stamp, et al., "Effects of Changing from Oral to Subcutaneous Methotrexate on Red Blood Cell Methotrexate Ployglutamate Concentrations and Disease Activity in Patients with Rheumatoid Arthritis," The Journal of Rheumatology, 2011, pp. 2539-2547, vol. 38, issue 12.

Pincus, et al., "Update on Methotrexate as the Anchor Drug for Rheumatoid Arthritis," Bulletin of the Hospital for Joint Diseases, 2013, pp. S9-S19, vol. 71.

Tudan, et al., "Selective Inhibition of Protein Kinase C, Mitogen-Activated Protein Kinase, and Neutrophil Activiation in Response to Calcium Pyrophosphate Dihydrate Crystals, Formyl-Methionyl-Leucyl-Phenylalanine, and Phorbol Ester by O-(Chloroacetyl-carbamoyl) fumagillol," Biochemical Pharmacology, 1999, pp. 1869-1880.

Tudan, et al., "The effect of inhibition toisomerase I and II on the anti-apopototic response associated with pro-inflammatory crystals of calcium pyrophosphate dihydrate in human neutrophils," Inflammation Research, 2003, pp. 8-17, vol. 52.

Verdrengh, et al., "Total abrogation of collagen II-induced arthritis and the B cell response to type II collagen using suboptimal doses of a toisomerase II antagonist," Ann. Rheum. Dis., 2002, pp. 829-831, vol. 61.

Weinman, et al., "Delayed neutrophil apoptosis in very early rheumatoid arthritis patients is abrogated by methotrexate therapy," Clinical and Experimental Rheumatology, 2007, pp. 885-887, vol. 25.

Wright, et al., "Novobiocin: Serum Concentrations and Urinary Excretion following Oral Administration in Man", Antibiotic Med, 1956, pp. 311-316, vol. 2., issue 5.

Spitzy et al. "The Distribution Volume of Some Antibiotics" 1957, pp. 996-1003, First Medical Department, University Hospital, Medical School. Vienna, Austria.

* cited by examiner

PHARMACEUTICAL COMPOSITION COMPRISING A COMBINATION OF METHOTREXATE AND NOVOBIOCIN, AND THE USE OF SAID COMPOSITION IN THERAPY

CROSS-REFERENCE TO RELATED APPLICATIONS

This application is a U.S. national phase application under 35 U.S.C. § 371 of International Application No. PCT/EP2018/064322, filed on May 31, 2018, which claims priority to Swedish Patent Application No. 1750688-2, filed May 31, 2017, the disclosure of which is hereby incorporated by reference in its entirety for all purposes.

FIELD OF THE INVENTION

The present invention relates to a pharmaceutical product comprising a combination of methotrexate and novobiocin, or any pharmaceutically acceptable salts of said compounds, and a pharmaceutical composition comprising (i) a therapeutic amount of methotrexate or any pharmaceutically acceptable salts thereof, and one or more pharmaceutically acceptable excipient, carrier or diluent, (ii) a non-therapeutic amount of novobiocin or any pharmaceutically acceptable salts thereof, and one or more pharmaceutically acceptable excipient, carrier or diluent. The invention further relates to a use of the pharmaceutical composition in therapy, such as prevention, progression prophylaxis and/or treatment of autoimmune diseases.

BACKGROUND OF THE INVENTION

The structure of the compound novobiocin (4-hydroxy-3-[4-hydroxy-3-(3-mehtylbut-2-enyl)benzamido]-8-methyl-coumarin-7-yl 3-O-carbamoyl-5,5-di-C-methyl-alpha-L-lyxofuranoside; NOV; CAS number 303-81-1) is:

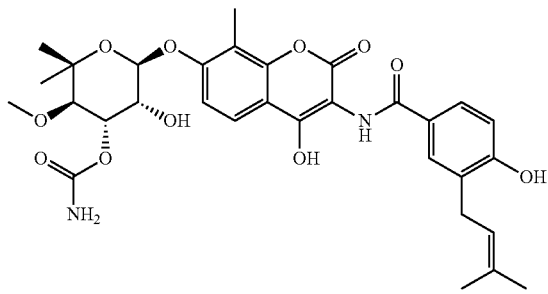

It is also known by the names: albamycin, cathomycin, streptonivicin, N-{7-[(3-O-carbamoyl-6-deoxy-5-methyl-4-O-methyl-beta-D-gulopyranosyl)oxy]-4-hydroxy-8-methyl-2-oxo-2H-chromen-3-yl}-4-hydroxy-3-(3-methylbut-2-en-1-yl)benzamide, cathocin, cardelmycin and antibiotic p.a. 93. Chemically, it consists of three separate moieties: the sugar noviose, a coumarin moiety and a benzoic acid derivative. This amino-coumarin was originally isolated from the *Streptomyces niveus* in the mid-1950s. Its initial antibiotic activity stems from its inhibition of topoisomerase II, e.g. of the GyrB subunit of bacterial DNA-gyrase, thus blocking the adenosine triphosphatase (ATPase)-catalyzed hydrolysis of ATP. It was launched as an antibiotic in the 1960s and used to treat staphylococcal infections and urinary tract infections caused by certain strains of *Proteus*. However, due to antibiotic resistance and subsequent loss of clinical efficacy it was eventually replaced with other antibiotics. Today, novobiocin is used in in vitro test kits to differentiate coagulase-negative staphylococci (CONS) in urine and to positively identify the *Staphylococcus saprophyticus* through its novobiocin resistance.

It has been shown in vivo in the mouse collagen-induced arthritis (CIA) model (Verdrengh et al. 2002) that topoisomerase II inhibitors at 12.5 mg/kg are able to significantly ameliorate experimental arthritis and that such inhibitors may be of use in the treatment of autoimmune diseases like rheumatic arthritis (RA). In addition, it has been shown that novobiocin is an inhibitor of the 90 kD heat shock protein (Hsp90) through binding to its C-terminus inducing degradation of the Hsp90 client proteins (Donnely A et al., 2008). The ATP-dependent Hsp90 is required for the refolding of denatured proteins following heat shock as well as the conformational maturation of several key proteins that are involved in cellular processes. The Hsp90 client proteins include several kinases, nitric-oxide synthase, androgen receptor, matrix metalloproteinase-2, oestrogen receptor, and others. Several of these client proteins are directly associated with the hallmarks of cancer and thus Hsp90 is a target for the development of cancer therapeutics. Hsp90-inhibitors are further thought to be useful as neuroprotective agents (e.g. Alzheimer's disease, ALS, Huntington's disease) as well as autoimmune disorders (e.g. multiple sclerosis). Novobiocin is an inhibitor of the ATP-dependent efflux transporter breast cancer resistance protein (BCRP) and the bile salt export pump (BSEP), as well as several organic anion transporters (OATs; e.g. OAT1, OAT3, and OAT4). The oral availability of novobiocin in rodents is about 30%. The oral bioavailability of novobiocin in humans is highly variable. Following oral administration of 0.25 to 2 g, an average Cmax of 10.9 to 65.7 mg/L is reached after approx. 1 to 4 h. About 3% of the dose is excreted unaltered in the urine (Wright W. W. et al., 1956). The liver is the main target organ for novobiocin metabolism, while bile is the main excretion pathway. Hepatic/biliary excretion is very rapid, irrespective of the route of administration, with about 30% of an oral dose excreted in the faeces. The parent is the predominant molecule in both tissues and fluids. Novobiocin is metabolized to a moderate degree and the quantitative metabolites in human, dog and cow have been shown to be comparable. Novobiocin is highly bound to plasma albumin in men (99.2%). In children, 15-45 mg/kg was the typical antibiotic dose; in adults, 1-2 g/day was the typical antibiotic dose, with a maximum tolerated dose (MTD) reported in adults of 4 g/day. The most common side effects in treated patients are loose stools/diarrhea, and nausea/vomiting. In oral dose levels above 10 mg/kg, skin rash due to hypersensitivity has been observed in 7 to 20% of the treated individuals.

The structure of the compound methotrexate (N-[4-[[(2,4-diamino-6-pteridinyl)methyl]methylamino]benzoyl]-L-glutamic acid; MTX; CAS number 59-05-2) is:

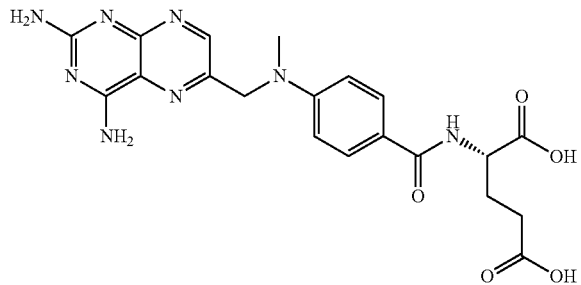 [SMILES: CN(Cc1cnc2nc(N)nc(N)c2n1)c1ccc(C(=O)N[C@@H](CCC(=O)O)C(=O)O)cc1]

This compound is also known by the names: (S)-2-{4-[(2,4-diamino-pteridin-6-ylmethyl)-methyl-amino]-benzoylamino}-pentanedioic acid; CL-14377; EMT-25299; antifolan N-[p-[[(2,4-diamino-6-pteridinyl)methyl]methylamino]benzoyl]-L-(+)-glutamic acid; (+)-amethopterin; L-amethopterin; amethopterin; amethopterine; 4-amino-10-methylfolic acid; emtexate; L-methotrexate; ledertrexate; metatrexan; methylaminopterin; mexate; NSC-740; and R-9985.

Methotrexate was first disclosed in 1948 and in 1956 it was shown to be superior to the then leading treatment of acute lymphocytic leukemia (ALL). In 1964, it was shown that methotrexate at the maximum tolerated dose (MTD) could successfully treat choriocarcinoma. Today, high dose levels of methotrexate, either as a single or combination treatment, are used to treat cancers like breast cancer, leukemia, ALL, gastric cancer, lung cancer, bladder cancer, head and neck cancer, non-Hodgkin lymphoma, germ cell tumors and osteogenic sarcoma (OS). It is cytotoxic to tumor cells through inhibition of dihydrofolate reductase (DHFR), an enzyme needed to produce essential cofactors for nucleotide biosynthesis, particularly thymidine. The depletion of nucleotides essential for DNA synthesis and cell division, result in apoptosis of the tumor cells. Methotrexate is taken up by the tumor cells via the low pH folate transporter (FR) and the reduced folate carrier (RFC). Synovial tissue from patients with rheumatoid arthritis express FRs and it is believed that these serve as a significant conduit for methotrexate influx.

In the cell, methotrexate is polyglutamated by folylpolyglutamate synthetase (FPGS) that is present both in the cytoplasm and the mitochondria. It has been suggested that the rate of polyglutamation in healthy (resting) cells in comparison to inflammatory (activated) cells is lower. Tumor methotrexate resistance and treatment failure have been shown to be due to altered expression levels and/or function of methotrexate uptake transporters, as well as decreased polyglutamylation and DHFR expression. Methotrexate is metabolized to 7-hydroxy-methotrexate in the liver by aldehyde oxidase and degraded to 2,4-diamino-$N^{10}$-methylpteroic acid (DAMPA) and glutamic acid by carboxypeptidase of intestinal bacteria and eliminated via the urine and the faeces.

In the early 1960s rheumatologists and dermatologists found that low doses of methotrexate, typically between 15 and 30 mg per week, had positive effects on rheumatoid arthritis, psoriasis and psoriatic arthritis. Today, methotrexate is known to be highly effective in the treatment and/or prophylaxis of progression and/or the general prophylaxis of several different autoimmune diseases, for example rheumatoid arthritis (RA), juvenile idiopathic arthritis (JIA), ankylosing spondylitis (AS), psoriasis (Pso), psoriatic arthritis (PsA), ulcerative colitis (UC) or Crohn's disease (CD). It is one of the most widely used small molecule disease-modifying antirheumatic drugs (DMARDs), either as stand-alone therapy or in combination with glucocorticoids (GCs) and/or in combination with other small molecule DMARDs, such as sulfasalazine and/or hydroxychloroquin and/or biological DMARDs, such as anti TNF-alpha biologics (for example infliximab, golimumab and adalimumab). The aetiology of autoimmune diseases as well as the precise mechanism of action (MoA) of methotrexate in autoimmune disease is unclear. However, the MoA of methotrexate is believed to be different in RA from its MoA in cancer. After uptake in for example lymphocytes, a cell type involved in inflammation, methotrexate interferes with the pyrimidine and purine de novo syntheses, required for DNA and RNA syntheses, thus inhibiting the proliferation of these cells. In addition, methotrexate modulates the release of endogenous, anti-inflammatory adenosine. Furthermore, methotrexate inhibits cytokine production/upregulation induced by activated T-cells. It also effects the expression of cell adhesion molecules (CAMs), which play an important role in the mediation between leukocyte and endothelial cell interactions. Leukocyte extravasation through the endothelial barrier is known to play an important role in the pathogenesis of rheumatoid arthritis. Methotrexate may also be used to terminate pregnancies, generally in combination with misoprostol. Methotrexate can be administered both orally as well as parenteral (subcutaneous, intramuscular or intravenous), intranasal or through inhalation.

Adverse reactions observed with methotrexate treatment of autoimmune diseases include GI disorders (e.g. abdominal pain, nausea), abnormal liver function (e.g. increases in alanine aminotransferase, aspartate aminotransferase, bilirubin, alkaline phosphatase), leukopenia, anaemia, thrombopenia, headache, tiredness, drowsiness, pneumonia, eosinophilia, oral ulcers, diarrhoea, exanthema, erythema and pruritus. In patients suffering from autoimmune disease, for example RA, guided by both tolerability and efficacy, methotrexate is typically administered at dose levels of 15 to 30 mg per week, either orally as tablets or syrup or subcutaneously with the use of for example prefilled syringes or autoinjectors. The systemic bioavailability of methotrexate in man after administration of an oral dose is relatively high (approximately 73%). However, the plasma concentrations of methotrexate exhibit wide variability. The bioavailability following subcutaneous (sc) administration is approx. 95% and the plasma variability as compared to oral administration is greatly reduced. In a clinical study that compared the efficacy of the dosing strength 15 mg/wk (Braun et al. 2008), the sc application route resulted in a significantly improved treatment success (34% of the RA patients vs. 24% for the oral application route). Reduced folate carriers (RFCs) are also expressed on both the apical and basolateral membranes of the gastrointestinal tract, and proton coupled folate transporter/haem carrier protein (PCFT/HCP1) are expressed on the apical membranes of enterocytes in the GI tract. The intestinal absorption of methotrexate is mediated by both. In addition to these influx transporters, methotrexate is a substrate of organic anion transporters (OATs), including OAT 1 and OAT 3, which are involved in the renal tubular secretion of methotrexate. Furthermore, it is a substrate of several ATP-dependent efflux transporters (ABC transporters), including P-glycoprotein (P-gp), breast cancer resistance protein (BCRP) and multidrug resistance-associated proteins (MRPs). These efflux transporters are expressed on several cell types throughout the body and play a role in the limited absorption of methotrexate from the GI tract and its rapid elimination from cells, i.e. non-polyglutamated methotrexate is transported out from the cell and excreted in the urine within the first 12 h after administration. Co-administration of methotrexate with some of the marketed proton-pump inhibitors (e.g. omeprazole and pantoprazole) or with resveratrol results in an increased intestinal absorption of methotrexate and a decreased renal elimination through inhibition of BCRP, P-gp, OAT1 and OAT3 transporter proteins, leading to an increase in, possibly serious, adverse events. In 2012, the FDA updated the labeling of methotrexate to include this information.

The occurrence and severity of adverse events depends both on the dosage level and frequency of methotrexate administration. In about 30% of the patient population methotrexate treatment needs to be terminated due to intolerability to the therapeutically effective treatment dose level. These patients could benefit from a methotrexate treatment if the therapeutic efficacy of methotrexate could be improved, i.e. if a lower dose of methotrexate could achieve the same therapeutic efficacy as the currently available pharmaceutical compositions of and/or treatment regimens for methotrexate.

Holden et al., Cancer Chemother Pharmacol (1995), 36, p 165-171, discloses combinations of antifolates and topoisomerase II inhibitors for use in cancer treatment to achieve a synergistic effect—i.e. an effect larger than the sum of the effects shown for each single agent—of both mode of actions. The combination of a new compound PT523 (antifolate) with etoposide (topoisomerase II inhibitor) appears to accomplish a synergistic effect. Holden et al. further disclosed that the sequential administration of a therapeutic dose of methotrexate followed by a therapeutic dose of novobiocin in an in vivo mouse oncology model does not produce a synergistic effect, but rather the expected additive effect of the two agents in tumor growth inhibition. Furthermore, they show in an in vitro murine oncology cell model, that the observed cell killing following the application of the combination methotrexate and novobiocin does not originate from an improved potency of novobiocin, as the inhibition of the topoisomerase II enzyme is not increased. In their in vivo mouse study, the dose used for methotrexate is 2 mg/kg continuous infusion for seven days, while for novobiocin the dose used is 100 mg/kg intraperitoneal on days 7, 9 and 11. The ratio novobiocin to methotrexate is about 50 to 1. For a human of ca. 70 kg, this treatment schedule would translate to a dose level of methotrexate of about 140 mg per treatment with a total of 1 gram per 7-day treatment cycle and of novobiocin of about 7 g per treatment with a total of 21 gram per 5-day treatment cycle. Such dose levels are well above the MTDs for both methotrexate and novobiocin. Thus, the increased cell killing observed in the presence of the combination of methotrexate and novobiocin at these high dose levels in the in vitro model is most likely due to general cell toxicities.

WO 2001/0164214 discloses the use of therapeutically effective amounts of topoisomerase I and II inhibitors in treatment of autoimmune disease. Also disclosed are polymeric controlled release dosage forms that allow for controlled release, for the localized treatment of inflammatory disease, enabling effective therapeutic concentrations of the drug to be maintained at the site, while avoiding repeated dosing and high plasma drug concentrations. Time frames described for the release of the pharmaceutically active agent from the pharmaceutical compositions are 7 to 10 days, or longer. From the disclosure it is understood, that the polymeric formulation that delivers the local, controlled release of the topoisomerase inhibitor is the technical solution provided by inventors to circumvent the toxicity and tolerability issues that are expected to arise following their systemic administration using immediate release formulations. The application further discloses, that "Methotrexate is used in combination with a topoisomerase inhibitor for the treatment of arthritis, since methotrexate has been shown to increase topoisomerase inhibitor activity (Holden et al, 1995)". However, as discussed above, Holden in fact reveals that the combination of methotrexate with novobiocin does not increase its topoisomerase inhibitor activity. No efficacy data for novobiocin in inflammatory disease models are shown in the application. In fact, several topoisomerase I and II inhibitors are shown to be not effective and/or to be too toxic in the different assays exemplified in the application. Novobiocin has a very different chemical structure and mode of action from all the other topoisomerase inhibitors tested and it is not obvious from the examples in the application that any topoisomerase inhibitor would work. The application discloses no data or examples of the combination of methotrexate with a topoisomerase inhibitor and/or novobiocin. In fact, no data for added and/or synergistic therapeutic efficacy of combinations of topoisomerase inhibitors with other, commonly used anti-inflammatory drugs are disclosed.

SUMMARY OF THE INVENTION

It is an object of the present invention to at least partly overcome the above problems, and to provide an improved pharmaceutical composition useful for the prevention, progression prophylaxis and/or treatment of a disease in which modulation of the pyrimidine and purine de novo syntheses is beneficial, and/or prevention, progression prophylaxis and/or treatment of a disease in which modulation of the release of endogenous, anti-inflammatory adenosine is beneficial, and/or prevention, progression prophylaxis and/or treatment of a disease in which modulation of cytokine production/upregulation induced by activated T-cells is beneficial, and/or prevention, progression prophylaxis and/or treatment of a disease in which modulation of the expression of cell adhesion molecules (CAMs), which, for example, play an important role in the mediation between leukocyte and endothelial cell interactions is beneficial, and/or the prevention, progression prophylaxis and/or treatment of a disease in which modulation of auto inflammatory processes, such as in autoimmune diseases, is beneficial.

It has now been found, that the combination of methotrexate (a) at a low therapeutic dose with (b) novobiocin at dosage levels that (1) are devoid of anti-inflammatory effects and that (2) are well below its traditional anti-biotic dosage levels, leads to an increased clinical efficacy of methotrexate, while the tolerability to the treatment remains unchanged and/or is improved.

The invention relates to a pharmaceutical product comprising a combination of the compound methotrexate and the compound novobiocin, or any pharmaceutically acceptable salts of said compounds. In one aspect, the pharmaceutical product comprises a therapeutic amount of methotrexate or any pharmaceutically acceptable salts thereof and a non-therapeutic amount of novobiocin or any pharmaceutically acceptable salts thereof.

The invention relates to an immediate release pharmaceutical composition comprising (i) a therapeutic amount of methotrexate or any pharmaceutically acceptable salts thereof, (ii) a non-therapeutic amount of novobiocin or any pharmaceutically acceptable salts thereof, optionally in the association with one or more pharmaceutically acceptable excipient, carrier or diluent.

In an aspect, the pharmaceutical composition comprises or consists of 5 to 20 mg of methotrexate and 5 to 40 mg of novobiocin, or any pharmaceutically acceptable salts of said compounds. In another aspect, the pharmaceutical composition comprises or consists of 5 to 30 mg of methotrexate and 5 to 100 mg of novobiocin, or any pharmaceutically acceptable salts of said compounds. In a further aspect, the pharmaceutical composition comprises or consists of 5 to 45 mg of methotrexate and 5 to 130 mg of novobiocin, or any pharmaceutically acceptable salts of said compounds. In a further aspect, the pharmaceutical composition comprises or consists of 5 to 60 mg of methotrexate and 5 to 150 mg of novobiocin, or any pharmaceutically acceptable salts of said compounds.

In one aspect the immediate release pharmaceutical composition comprises or consists of 5 to 100 mg of methotrexate and 5 to 300 mg of novobiocin.

In another aspect, the immediate release pharmaceutical is for use in a dosage regime comprising administration of the composition to a mammal at the most once per week.

In yet another aspect, the immediate release pharmaceutical is for use in a dosage regime comprising administration of the composition to a mammal once every 7 to 10 days. In an aspect, the immediate release pharmaceutical is for use in a dosage regime comprising administration of the composition to a mammal once weekly.

In another aspect, the pharmaceutical composition comprises or consists of 5 to 20 mg, or 5 to 30 mg, or 15 to 30 mg of methotrexate and 5 to 100 mg, or 5 to 40 mg of novobiocin for use in a dosage regime comprising administration of the composition to a mammal once every 1 to 7 days, or 1 to 10 days, or once weekly.

In yet a further aspect, the pharmaceutical composition comprises or consists of 5 to 45 mg, or 22.5 to 45 mg of methotrexate and 5 to 130 mg, or 5 to 150 mg of novobiocin for use in a dosage regime comprising administration of the composition to a mammal once every 7 to 14 days or once every two weeks.

In a further aspect, the pharmaceutical composition comprises or consists of 5 to 60 mg, or 30 to 60 mg of methotrexate and 5 to 150 mg, or 5 to 200 mg of novobiocin for use in a dosage regime comprising administration of the composition to a mammal once every 7 to 21 days or once every three weeks.

In a further aspect, the pharmaceutical composition comprises or consists of 5 to 100 mg of methotrexate and 5 to 250 mg of novobiocin for use in a dosage regime comprising administration of the composition to a mammal once every 7 to 31 days or once every four weeks.

In one aspect, the ratio of of novobiocin to methotrexate ranges from about 0.05 to 100 molar equivalents. In another aspect, the ratio of the two compounds in the combination composition of the invention ranges from about 0.05 to 100 molar equivalents of novobiocin to methotrexate.

The new combination increases the concentration and/or the level of intracellular polyglutamated species of methotrexate in cell types involved in the perpetuation of the disease. It increases gastrointestinal absorption and/or decreases systemic clearance of methotrexate. The new combination facilitates the use of lower dosing strengths of methotrexate per dosing and/or a reduced dosing frequency. The combination is also believed to reduce general, and in particular gastrointestinal side effects and/or toxicity of methotrexate. The new combination is believed to improve clinical efficacy and/or responder rate. The new combination is expected to increase methotrexate treatment tolerability and/or reduce methotrexate treatment cessation and reduce interpatient treatment variability in response to methotrexate treatment.

The combination composition of the invention is expected to result in a significantly increased level and/or rate of formation of methotrexate-polyglutamate (MTX-PG) species with glutamate chains ≥3, and a comparable or decreased level and/or rate of MTX-PG species with glutamate chains <3 as compared to treatment with the presently marketed methotrexate products. The new combination increases the intracellular MTX-$PG_{3-5}$ to MTX-$PG_{1-2}$ ratio.

In the combination composition of the invention, the cumulative methotrexate dose needed for clinical efficacy is ≤95%, or ≤90%, or ≤80%, or ≤70% as compared to treatment with the presently marketed methotrexate products.

In the new combination, the tolerability to methotrexate treatment (i.e. efficacy versus toxicity) is expected to be increased significantly as compared to treatment with the presently marketed methotrexate product. In the combination composition of the invention, the tolerability to methotrexate treatment (i.e. efficacy versus toxicity) is expected to be increased ≥10%, or ≥20% or ≥30% as compared to treatment with the presently marketed methotrexate products.

In the new combination, treatment withdrawal is expected to be decreased significantly as compared to treatment with the presently marketed methotrexate product. In the combination composition of the invention, treatment withdrawal is expected to decrease by ≥10% or ≥25% as compared to treatment with the presently marketed methotrexate products.

With the new combination, treatment compliance is expected to increase significantly as compared to treatment with the presently marketed methotrexate products. With the combination composition of the invention, treatment compliance is expected to increase by ≥10% or ≥25% as compared to treatment with the presently marketed methotrexate products.

The invention also relates to a process for the preparation of a pharmaceutical composition, which comprises mixing methotrexate with novobiocin and a pharmaceutically acceptable adjuvant, diluent or carrier.

The pharmaceutical composition may comprise of two separate compositions wherein one composition comprises a therapeutic amount of methotrexate or any pharmaceutically acceptable salts thereof and the second composition comprises a non-therapeutic amount of novobiocin or any pharmaceutically acceptable salts thereof, for conjoint treatment. Such conjoint treatment may be achieved by way of the simultaneous, sequential or separate dosing of the individual compositions for the prevention, progression prophylaxis and/or treatment defined herein.

In one aspect, the invention relates to a pharmaceutical composition comprising (i) a therapeutic amount of methotrexate or any pharmaceutically acceptable salts thereof, and optionally one or more pharmaceutically acceptable excipient, carrier or diluent, and (ii) a non-therapeutic amount of novobiocin or any pharmaceutically acceptable salts thereof, and optionally one or more pharmaceutically acceptable excipient, carrier or diluent.

The pharmaceutical composition may comprise of one composition comprising a therapeutic amount of methotrexate or any pharmaceutically acceptable salts thereof together with a non-therapeutic amount of novobiocin or any pharmaceutically acceptable salts thereof, for conjoint treatment. In another aspect, the invention relates to a pharmaceutical composition comprising (i) a therapeutic amount of methotrexate or any pharmaceutically acceptable salts thereof, (ii) a non-therapeutic amount of novobiocin or any pharmaceutically acceptable salts thereof, and (iii) one or more pharmaceutically acceptable excipient, carrier or diluent.

In one aspect, the ratio of novobiocin to methotrexate in the immediate release pharmaceutical composition as defined above, ranges from about 0.05 to 100 molar equivalents for per oral administration. In another aspect, the ratio of novobiocin to methotrexate in the immediate release pharmaceutical composition as defined above, ranges from 2 to 20 molar equivalents for per oral administration. In a preferred aspect, the ratio of novobiocin to methotrexate in the immediate release pharmaceutical composition as defined above, ranges from 5 to 20 molar equivalents for per oral administration.

In another aspect, the ratio of novobiocin to methotrexate in the immediate release pharmaceutical composition as defined above, ranges from about 0.05 to 50 molar equivalents for parenteral administration. In another aspect, the ratio of novobiocin to methotrexate in the immediate release pharmaceutical composition as defined above, ranges from 0.1 to 10 molar equivalents for parenteral administration. In a preferred aspect, the ratio of novobiocin to methotrexate in the immediate release pharmaceutical composition as defined above, ranges from 1 to 10 molar equivalents for parenteral administration.

The pharmaceutical composition may be administered orally or parenterally. A parenteral product may be administered subcutaneous or intravenous. In one aspect, the pharmaceutical composition defined above is a soft gel capsule (SGC) for oral administration or a solution for parenteral administration.

In one aspect, the pharmaceutical composition as defined above comprises
  a. about 1 to about 50 wt % of methotrexate or a pharmaceutically acceptable salt thereof;
  b. about 0.5 to about 50 wt % of novobiocin or a pharmaceutically acceptable salt thereof;
  c. a solvent sterile water for injection USP 10 to 98% by weight of the total composition and water being present in an amount from about 1 up to 100 wt %;
  d. an isotonization agent, such as sodium chloride or potassium chloride;
  e. an ionization agent, such as sodium hydroxide; and
  f. optionally other excipients, such as, solvents, preservation agents, pH adjusting agents, solubilizers, co-solvents and combinations thereof,
whereby weight percentages are percentages of the total weight of the composition.

In a further aspect, the pharmaceutical composition may comprise
  a. about 1 to about 5 wt % of methotrexate sodium;
  b. about 1 to about 10 wt % of novobiocin sodium;
  c. a solvent sterile water for injection USP 84 to 97.5% by weight of the total composition and water being present in an amount from about 1 up to 100 wt %; and
  d. about 0 to 1 wt % NaCl;
whereby weight percentages are percentages of the total weight of the composition.

The solution may have a pH from about 6.5 to about 9.

In another aspect, the pharmaceutical composition comprises or contains the pharmaceutical composition as defined in the paragraph above in a container, such as a carpoule, an ampoule, a syringe or an autoinjector.

In a further aspect, the pharmaceutical composition may comprise
  a. about 1 to about 5 wt % of methotrexate;
  b. about 1 to about 10 wt % of novobiocin;
  c. a solvent sterile water for injection USP 84 to 97.5% by weight of the total composition and water being present in an amount from about 1 up to 100 wt %; and
  d. about 0 to 1 wt % NaCl;
  e. about 0 to 1 wt % NaOH;
  f. about 0 to 1 wt % HCl;
whereby weight percentages are percentages of the total weight of the composition.

The solution may have a pH from about 6.5 to about 9.

In another aspect, the pharmaceutical composition comprises or contains the pharmaceutical composition as defined in the paragraph above in a container, such as a carpoule, an ampoule, a syringe or an autoinjector.

In one aspect, the pharmaceutical composition as defined above comprises
  a. about 0.5% to about 50 wt % of methotrexate or a pharmaceutically acceptable salt thereof;
  b. about 0.5% to about 50 wt % of novobiocin or a pharmaceutically acceptable salt thereof;
  c. a solvent including a polyethylene glycol with a molecular weight ranging from 200 to 1500, poloxamers, propylene glycol, glycerin, or low molecular weight alcohols (e.g. ethanol) and water, or a combination thereof up to 100 wt %;
  d. a solubility enhancer, such as an ionizing agent, including metal hydroxides (e.g. NaOH, KOH, NH$_4$OH, Ca(OH)$_2$, Al(OH)$_3$ and Mg(OH)$_2$), HCl, HBr, HI, H$_2$SO$_4$, acetic acid, butanoic acid, citric acid, fumaric acid, lactic acid, maleic acid, malic acid, propionic acid, pyruvic acid, and sulfonates (e.g. methane-, ethane- or benzene sulfonates) in 0.2 and 2.4 mole equivalents per combined mole equivalent of methotrexate and novobiocin, and/or polyvinylpyrrolidinone (PVP), and/or polysorbates, and/or vitamin E TPGS;
  e. an ionizing agent, such as sodium hydroxide; and
  f. optionally other excipients, such as solvents, co-solvents, preservation agents, plasticizers, pH adjusting agents, solubilizers, opacifiers, colorants, humectants, flavoring agents, and combinations thereof,
whereby weight percentages are percentages of the total weight of the composition.

In a further aspect, the pharmaceutical composition may comprise
  a. about 0.75 to about 17.5 wt % of methotrexate sodium;
  b. about 0.75 to about 42.5 wt % of novobiocin sodium;
  c. about 0 to 20 wt % water;
  d. about 0 to 15 wt % ethanol;
  e. about 0 to 3 wt % polyvinylpyrrolidinone;
  f. about 0 to 15 wt % vitamin E TPGS;
  g. about 0 to 3 wt % propylene glycol;
  h. about 0 to 3 wt % lactic acid
  i. about 0 to 10 wt % polysorbate 20 or 80
  j. about 0 to 70 wt % PEG400
  k. about 0 to 80 wt % PEG600
whereby weight percentages are percentages of the total weight of the composition.

The liquid matrix may have a pH from about 2.5 to about 7.5.

In another aspect, the pharmaceutical composition comprises or contains the pharmaceutical composition as defined in the paragraph above in Gelatin coating of either Type A or Type B.

The invention also relates to a dosage regime for administration of the pharmaceutical composition as defined above, comprising administration of the composition once every 7, 10, 14, 21 or 28 days.

A dosage regime for once weekly administration may comprise 5 to 30 mg of methotrexate and 5 to 100 mg of novobiocin. A dosage regime for once every two weeks may comprise 5 to 45 mg of methotrexate and 5 to 130 mg of novobiocin. A dosage regime for once every three weeks may comprise 5 to 60 mg of methotrexate and 5 to 150 mg of novobiocin. A dosage regime for once every four weeks may comprise 5 to 100 mg of methotrexate and 5 to 250 mg of novobiocin.

It is well known, that compliance to a treatment is inversely correlated to the dosing frequency. The posology of currently marketed methotrexate-containing pharmaceutical products foresees a dosing schedule of once or twice weekly. It would be beneficial to reduce the frequency of dosing. This would improve patient compliance and is believed to reduce side effects. It also reduces overall cost for health care.

The invention relates to the pharmaceutical product as defined above, or the immediate release pharmaceutical composition as defined above for use in therapy.

One aspect relates the pharmaceutical product as defined above, or the pharmaceutical composition as defined above for use in the prevention, progression prophylaxis and/or treatment of a disease in which modulation of the pyrimidine and purine de novo syntheses is beneficial and/or the release of endogenous, anti-inflammatory adenosine and/or cytokine production/upregulation and/or CAMs expression is beneficial and/or modulation of a persistent anti-inflammatory cell response is beneficial, such as an autoimmune diseases.

Another aspect relates the pharmaceutical product as defined above, or the pharmaceutical composition as defined above for use in the prevention, progression prophylaxis and/or treatment of arthritides, such as osteoarthritis, osteoarthrosis, idiopathic inflammatory arthritides of whatever joint distribution and associated syndromes, reactive arthritis, rheumatoid arthritis, psoriatic arthritis, polymalgia rheumatic, rheumatic fever and its systemic complications, oligoarthritis, microscopic poly-arteritis, Takayasu's arteritis, septic arthritis, or the active juvenile idiopathic form thereof and Stills' disease.

One aspect relates the pharmaceutical product as defined above, or the pharmaceutical composition as defined above for use in the prevention, progression prophylaxis and/or treatment of both primary and secondary to dysplasia, such as congenital hip dysplasia, cervical and lumbar spondylitis, low back and neck pain, undifferentiated spondyloarthropathy, infection-related arthopathies and bone disorders, such as tuberculosis, Potts' disease and Poncet's syndrome, acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma, mixed connective tissue disease, and undifferentiated connective tissue disease, inflammatory myopathies including dermatomyositis and polymyositis, and, vasculitides including giant cell arteritis, Churg-Strauss syndrome, polyarteritis nodos, microscopic poly-arteritis, and vasculitides associated with viral infection, hypersensitivity reactions, cryoglobulins, and paraproteins, Familial Mediterranean fever, Muckle-Wells syndrome, and Familial Hibernian fever, Kikuchi disease; drug-induced arthralgia, tendonitides, and myopathies.

An active juvenile form of any of these diseases may exist and any such juvenile form is included in any of the mentioned diseases.

Another aspect relates the pharmaceutical product as defined above, or the pharmaceutical composition as defined above for use in the prevention, progression prophylaxis and/or treatment of rheumatoid arthritis or the active juvenile idiopathic form thereof and Stills' disease.

A further aspect relates the pharmaceutical product as defined above, or the pharmaceutical composition as defined above for use in the prevention, progression prophylaxis and/or treatment of oligoarthritis or the active juvenile idiopathic form thereof.

An aspect relates the pharmaceutical product as defined above, or the pharmaceutical composition as defined above for use in the prevention, progression prophylaxis and/or treatment of polyarthritis or the active juvenile idiopathic form thereof.

One aspect relates the pharmaceutical product as defined above, or the pharmaceutical composition as defined above for use in the prevention, progression prophylaxis and/or treatment of psoriatic arthritis or the active juvenile idiopathic form thereof.

Yet another aspect relates the pharmaceutical product as defined above, or the pharmaceutical composition as defined above for use in the prevention, progression prophylaxis and/or treatment of psoriasis, plaque psoriasis or the active juvenile idiopathic form thereof.

Yet a further aspect relates the pharmaceutical product as defined above, or the pharmaceutical composition as defined above for use in the prevention, progression prophylaxis and/or treatment of dermatological diseases, including, but not limited to pemphigus vulgaris, pyoderma gangrenosum, dermatitis herpetiformis, alopecia areata, lichen planus, corticosteroid-dependent chronic idiopathic urticaria, plaque psoriasis, cutaneous lupus erythematosus and atrophy blanche.

Another aspect relates the pharmaceutical product as defined above, or the pharmaceutical composition as defined above for use in the prevention, progression prophylaxis and/or treatment of inflammatory bowel diseases, including eosinophilic gastro-enteritis, mastocytosis, Crohn's disease, colitis, including ulcerative colitis, proctitis, coeliac disease, irritable bowel syndrome and food-related allergies, which may have effects remote from the gut, such as migraine, rhinitis or eczema.

Yet another aspect relates the pharmaceutical product as defined above, or the pharmaceutical composition as defined above for use in the prevention, progression prophylaxis and/or treatment of Crohn's disease and ulcerative colitis including juvenile idiopathic forms thereof.

One aspect relates the pharmaceutical product as defined above, or the pharmaceutical composition as defined above for use in the prevention, progression prophylaxis and/or treatment of systemic or cutaneous lupus erythematosus.

An aspect relates the pharmaceutical product as defined above, or the pharmaceutical composition as defined above for use in the prevention, progression prophylaxis and/or treatment of glioma.

An aspect relates the pharmaceutical product as defined above, or the pharmaceutical composition as defined above for use in the prevention, progression prophylaxis and/or treatment of cancers, such as breast cancer, leukemia, acute lymphoblastic leukemia (ALL), gastric cancer, lung cancer, bladder cancer, head and neck cancer, non-Hodgkin lymphoma, germ cell tumors and osteogenic sarcoma (OS)

An aspect relates the pharmaceutical product as defined above, or the pharmaceutical composition as defined above for use in terminating pregnancies, optionally in combination with misoprostol.

In one aspect a dosage regime for administration of the pharmaceutical composition as defined above, comprises or consists of administration of the composition once every week.

In another aspect a dosage regime for administration of the pharmaceutical composition as defined above, comprises or consists of administration of the composition once every two weeks.

In a further aspect a dosage regime for administration of the pharmaceutical composition as defined above, comprises or consists of administration of the composition once every three weeks.

In an aspect a dosage regime for administration of the pharmaceutical composition as defined above, comprises or consists of administration of the composition once every four weeks.

In one aspect a dosage regime for administration of the pharmaceutical composition as defined above, comprises or consists of administration of the composition once every 10, or 20, or 30 days.

In a further aspect a dosage regime for administration of the pharmaceutical composition as defined above, comprises or consists of administration of the composition once every month.

The invention also relates to a method of treating, preventing or reducing the risk of a disease in which modulation of the pyrimidine and purine de novo syntheses, and/or the release of endogenous, anti-inflammatory adenosine, and/or cytokine production/upregulation induced by activated T-cells and/or the expression of cell adhesion molecules (CAMs) and/or extra-cellular levels of (chemotactic) cytokines and/or the modulation of a persistent anti-inflammatory cell response is beneficial, which comprises administering to a mammal, such as a human, in need thereof, a pharmaceutical composition comprising a combination of methotrexate and novobiocin, or any pharmaceutically acceptable salts of said compounds.

In one aspect of the method, the pharmaceutical composition comprises a therapeutically effective amount of 5 to 100 mg of methotrexate and a therapeutically inactive amount of 5 to 300 mg of novobiocin. In another aspect of the method, the disease is one or more autoimmune disease.

In a further aspect of the method, the disease is any one of the diseases mentioned above.

The invention also relates to a use of the pharmaceutical product as defined above, or the pharmaceutical composition as defined above, in the prevention, progression prophylaxis and/or treatment of a disease in which modulation of the pyrimidine and purine de novo syntheses is beneficial and/or the release of endogenous, anti-inflammatory adenosine and/or cytokine production/upregulation and/or CAMs expression is beneficial and/or modulation of a persistent anti-inflammatory cell response is beneficial, such as an autoimmune diseases, any one of the diseases mentioned above.

The invention also relates to a use of the pharmaceutical product as defined above, or the pharmaceutical composition as defined above, in the manufacture of a medicament for the prevention, progression prophylaxis and/or treatment of a disease in which modulation of the pyrimidine and purine de novo syntheses is beneficial and/or the release of endogenous, anti-inflammatory adenosine and/or cytokine production/upregulation and/or CAMs expression is beneficial and/or modulation of a persistent anti-inflammatory cell response is beneficial, such as an autoimmune diseases, or any one of the diseases mentioned above.

The prevention, progression prophylaxis and/or treatment defined herein may be applied as a sole therapy of the combination of the invention or may involve, in addition to the combination of the invention, conjoint treatment with other conventional therapies of value in treating one or more disease conditions referred to herein.

Such conventional therapy may include one or more of the following categories of agents: non-steroidal anti-inflammatory agents (hereinafter NSAIDs), whether applied topically or systemically, including non-selective cyclo-oxygenase COX-1/COX-2 and selective COX-2 inhibitors (such as meloxicam, celecoxib, rofecoxib, valdecoxib, lumarocoxib, parecoxib and etoricoxib), piroxicam, diclofenac, propionic acids (such as naproxen), flurbiprofen, fenoprofen, ketoprofen and ibuprofen, fenamates (such as mefenamic acid), indomethacin, sulindac, ayapropayone, pyrayoleones (such as phenylbutazone), salicylates (such as aspirin); cyclo-oxygenase inhibiting nitric oxide donors (CI-NODs; such as naproxinod); glucocorticosteroids (GCS), whether administered by topical, oral, intramuscular, intravenous, or intra-articular routes, (such as flunisolide, triamcinolone acetonide, betamethasone dipropionate, budesonide, fluticasone propionate, ciclesonide or mometasone furoate); small-molecule disease modifying agents (DMARD) such as sulfasalazine, leflunomide, hydroxychloroquine, d-penicillamine; auranofin and other parenteral or oral gold preparations; nutritional supplements such as glucosamine; agonists or antagonists of cytokine function, (including agents which act on cytokine signaling pathways such as modulators of the SOCS system) including alpha-, beta-, and gamma-interferons; insulin-like growth factor type I (IGF-I); interleukins (IL) including IL-1 to 23, and interleukin antagonists or inhibitors (for example diacerein, anakinra, secukinumab, ixekizumab); tumor necrosis factor alpha (TNF-α) inhibitors (such as infliximab, adalimumab, and golimumab) and TNF receptor antagonists including immunoglobulin molecules (such as etanercept) and low-molecular-weight agents such as pentoxifylline; monoclonal antibody targeting B-Lymphocytes (such as CD20 (rituximab). MRA-alL16R and T-Lymphocytes, CTLA4-Ig; HuMax 11-15); modulators of chemokine receptor function, such as an antagonist of CCR2, CCR2A, CCR2B, CCR3, CCR4, CCR5, CCR6, CCR7, CCR8, CCR9, CCRIO and CCRI I (for the C-C family); CXCRI, CXCR2, CXCR3, CXCR4 and CXCR5 (for the C-X-C family) and $CX_3CRI$ for the $C-X_3-C$ family; inhibitors of matrix metalloprotease $(Tv-IMPs)_5$ i.e., the stromefysins, the collagenases, and the gelatinases, as well as aggrecanase; especially collagenase-1 (MMP-I), collagenase-2 (MMP-8), collagenase-3 (MMP-13), stromelysin-1 (MMP-3), stromelysin-2 (MMP-IO), and stromelysin-3 (MMP-11) and MMP-9 and MMP-12, including agents such as doxycycline; leukotriene biosynthesis inhibitors, 5-lipoxygenase (5-LO) inhibitors or 5-lipoxygenase activating protein (FLAP) antagonists; zileuton; ABT-761; fenleuton; tepoxalin;

Abbott-79175; Abbott-85761; N-(5-substituted)-thiophene-2-alkylsulfonamide; 2,6-di-tert-butylphenolhydrazones, methoxytetrahydropyrans [e.g. ZD-213S]; SB-210661; pyridinyl-substituted 2-cyanonaphthalene compounds [e.g. L-739,010]; 2-cyanoquinoline compounds [e.g.

L-746,530]; indole or quinoline compounds [e.g. MK-591, MK-886, and BAYx1005]; receptor antagonists for leukotrienes (LT) B4, LTC4, LTD4, and LTE4 (such as phenothiazin-3-Is [e.g. L-651,392], amidino compounds [e.g. CGS-25019c], benzoxalamines [e.g. ontazolast], benzenecatboximidamides [e.g. BIIL 284/260], zafirlukast, ablukast, montelukast, pranlukast, verlukast (MK-679), RG-12525, Ro-245913, iralukast (CGP 45715A), and BAYx7195; phosphodiesterase (PDE) inhibitors, such as a methylxanthanine [e.g. theophylline, propentofylline and aminophylline], selective PDE isoenzyme inhibitors including inhibitors of the isoform PDE4D [e.g. apremilast] or inhibitors of PDE5; organophosphate acetylcholinesterase inhibitors (such as metrifonate); endothelin antagonists (such as tezosentan, bosentan, macitentan, enrasentan, and sixtasentan); angiotensin II antagonists (such as azilzartan, losartan, candesartan, and telmisartan); dual antagonists for both angiotensin II and endothelin A receptors (DARAs) such as disclosed in WO2000001389 and WO2001044239; histamine type 1 receptor antagonists (such as cetirizine, loratadine, desloratadine, fexofenadine, acrivastine, terfenadine, astemizole, azelastine, levocabastine, chlorpheniramine, promethazine., cyclizine, or mizolastine), applied orally, topically or parenterally; histamine type 4 receptor antagonists; proton pump inhibitors (such as omeprazole) or a gastroprotective histamine type 2 receptor antagonists; alpha-1/alpha-2 adrenoceptor agonist vasoconstrictor sympathomimetic agents (such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, or tramazoline hydrochloride); anticholinergic agents including muscarinic receptor (M1 M2, and M3) antagonist (such as atropine, scopolamine, glycopyrrolate, ipratropium bromide, tiotropium bromide, oxitropium bromide, pirenzepine or telenzepine); beta-adrenoceptor (including beta receptor subtypes 1-4) agonists (such as isoprenaline, salbutamol, formoterol, salmeterol, terbutaline, orciprenaline, bitolterol mesylate, or pirbuterol, or a chiral enantiomer thereof); chromones (such as sodium cromoglycate or nedocromil sodium); agents that modulate a nuclear hormone receptor such as PPARs; immunoglobulin (Ig) or Ig preparations or antagonists or monoclonal antibodies modulating Ig function such as anti-IgE (such as omalizumab); systemic or topically-applied anti-inflammatory agents (such as thalidomide or a derivative thereof, a retinoid, dithranol or calcipotriol); combinations of aminosalicylates and sulfapyridine (such as mesalazine, balsalazide, and olsalazine); immunomodulatory agents such as the thiopurines, e.g. adenosine Ata agonists (such as CGS-21680), adenosine A3 agonists (such as IB-MECA) and adenosine A1b antagonists; antibacterial agents such as a penicillin derivative, a tetracycline, a macrolide, a beta-lactam, a fluoroquinolone, metronidazole, an inhaled aminoglycoside; an antiviral agent (such as acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine); or a non-nucleoside reverse transcriptase inhibitor (such as nevirapine or efavirenz); cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor; CNS agents such as an antidepressants (such as sertraline), anti-Parkinsonian drugs (such as deprenyl, L-dopa, ropinirole, pramipexole), MAOB inhibitors (such as selegine and rasagiline), comP inhibitors (such as tasmar), A-2 inhibitors, dopamine reuptake inhibitors, NMDA antagonists, nicotine agonists, dopamine agonists or antagonists, anti-Alzheimer's drugs (such as donepezil, rivastigmine, tacrine); agents for the treatment of acute or chronic pain (such as a centrally or peripherally-acting analgesics [e.g. an opioid or derivative thereof], carbamazepine, phenytoin, sodium valproate, amitryptiline, paracetamol, or a non-steroidal anti-inflammatory agent), parenterally or topically-applied (including inhaled) local anesthetic agents (such as lignocaine or a derivative thereof); anti-osteoporosis agents, including a hormonal agent (such as raloxifene), and biphosphonates (such as alendronate); tryptase inhibitors; platelet activating factor (PAF) antagonists; interleukin converting enzyme (ICE) inhibitors; IMPDH inhibitors; adhesion molecule inhibitors including VLA-4 antagonists; cathepsin; kinase inhibitors such as an inhibitor of tyrosine kinase (such as Btk, Itk, Jak3 or MAP, [e.g. tofacitinib, gefitinib or imatinib mesylate]), a serine/threonine kinase inhibitors (such as an inhibitor of a MAP kinase such as p38, INK, protein kinase A, B or C, or inhibitors of kappaB kinases, such as IKK1 IKK2 or IKK3), or modulators of kinases involved in cell cycle regulation; glucose-6 phosphate dehydrogenase inhibitors; kinin-$B_1$- or $B_2$-receptor antagonists; anti-gout agents (such as colchicine); xanthine oxidase inhibitors (such as allopurinol); uricosuric agents (such as probenecid, sulfinpyrazone or benzbromarone); growth hormones (such as growth hormone secretagogues); transforming growth factor (TGFβ); platelet-derived growth factor (PDGF); fibroblast growth factor (such as basic fibroblast growth factor (bFGF)); granulocyte macrophage colony stimulating factor (GM-CSF); capsaicin cream; tachykinin $KK_1$. or $NK_3$. receptor antagonists (such as NKP-608C, SB-233412 (talnetant) or D-441S); elastase inhibitor (such as LT-77 or ZD-0892); TNF-alpha converting enzyme inhibitors (TACE); induced nitric oxide synthase (iNOS) inhibitors; chemoattractant receptor-homologous molecule expressed on TH2 cells, (such as a CRTH2 antagonists); inhibitors of P38; modulators of the function of Toll-like receptors (TLR), modulators of the activity of purinergic receptors such as P2X7; or inhibitors of transcription factor activation (such as NFkB, API, or STATS), agents modulating guanylate cyclase (such as riociguat); agents for the treatment of cancer, for example suitable agents include: an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil ortegafur, raltitrexed, cytosine arabinoside, hydroxyurea, gemcitabine or paclitaxel); an antitumor antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, fhitamide, nilutamide or cyproterone acetate), a LHRH antagonist or LHRH agonist (for example goserelin, leuprorelin or biiserelin), a progestogen (for example megestrol acetate), an aromatase inhibitor (for example as anastrozole, letrozole, vorazole or exemestane) or an inhibitor of 5α-reductase such as finasteride; an agent which inhibits cancer cell invasion (for example a metalloproteinase inhibitor like marimastat or an inhibitor of urokinase plasminogen activator receptor function); an inhibitor of growth factor function, for example: a growth factor antibody (for example the anti-erbb2 antibody trastuzumab, or the anti-erbbI antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZDI 839), N-(3-ethynylphenyl)-6,7-bis (2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family; an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin); a vascular damaging agent such as combretastatin A4, or a compound disclosed in WO 99/02166, WO 00/40529, WO 00/41669, WO 01/92224, WO 02/04434 or WO 02/08213; an agent used in antisense therapy, for example one directed to one of the targets listed above, such as ISIS 2503, an anti-ras antisense; an agent used in a gene therapy approach, for example approaches to replace aberrant genes such as aberrant p53 or aberrant BRCAI or BRCA2, GDEPT (gene-directed enzyme pro-drug therapy) approaches such as those using cytosine deaminase, thymidine kinase or a bacterial nitro-reductase enzyme and approaches to increase patient tolerance to chemotherapy or radiotherapy such as multidrug resistance gene therapy; or an agent used in an immunotherapeutic approach, for example ex-vivo and in-vivo approaches to increase the immunogenicity of patient tumor cells, such as transfection with cytokines such as IL-2, IL-4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

In another aspect, the invention relates to a pharmaceutical product comprising (1) the pharmaceutical composition as defined above, e.g. an immediate release pharmaceutical composition comprising (i) a therapeutic amount of methotrexate or any pharmaceutically acceptable salts thereof, (ii) a non-therapeutic amount of novobiocin or any pharmaceutically acceptable salts thereof, optionally in the association with one or more pharmaceutically acceptable excipient, carrier or diluent, (2) an additional therapeutic agent, or a pharmaceutically acceptable salt thereof, and, optionally, (3) one or more pharmaceutically acceptable excipient, carrier or diluent.

In one aspect, the invention relates to a conjoint treatment with (1) the pharmaceutical composition as defined above, and (2) an additional, conventional therapy, such as NSAIDs, GCSs, small molecule and/or biologic DMARDs, that are of value in treating one or more disease conditions referred to herein.

Such conjoint treatment may be achieved by way of the simultaneous, sequential or separate dosing of the individual components of the prevention, progression prophylaxis and/or treatment defined herein. Such combination compositions employ the pharmaceutical product as defined above, or the pharmaceutical composition as defined.

DETAILED DESCRIPTION OF PREFERRED ASPECTS OF THE INVENTION

Definitions

The definitions set forth in this application are intended to clarify terms used throughout this application.

The term "herein" means the entire application.

As used herein, the term "small molecule" refers to organic compounds with well-defined chemical structure that is independent of the manufacturing process and a maximum molecular weight of 1000 kD, and which may regulate one or several biological processes following the administration of a pharmaceutical composition comprising such a small molecule to a living organism, like a mammal.

As used herein, the term "disease" is intended to include disorder, condition or any equivalent thereof.

The term "immediate release" as used herein means a dissolution of methotrexate and novobiocin from the pharmaceutical composition within 30 minutes.

The term "MTX" as used herein means methotrexate. The term "NOV" as used herein means novobiocin.

As used herein, the term "patient" refers to a mammal, for example, a human.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer a clinically effective amount of methotrexate and a clinically ineffective amount of novobiocin, to mitigate either a pre-existing disease state, acute or chronic, or a recurring condition. This definition also encompasses prophylactic therapies for prevention of recurring conditions and continued therapy for chronic disorders.

As used herein, the terms "DMARD" or "disease modifying agent" refer to a category of drugs, that by their therapeutic use in autoimmune diseases (e.g. rheumatoid arthritis, Crohn's disease and psoriasis and their juvenile forms) slow down disease progression of such diseases.

As used herein, the term "optional" or "optionally" means that the subsequently described event or circumstance may but need not occur, and that the description includes instances where the event or circumstance occurs and instances where it does not.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio and/or that are approved or approvable by a regulatory agency or body, for example the Food and Drug Administration (FDA) or the European Medicines Agency (EMA).

As used herein, the term "salt" refer to forms of the disclosed compounds, wherein the parent compound is modified by making acid or base salts thereof, that possess the desired pharmacological activity of the parent compound. Generally, pharmaceutically acceptable salts of the compound of the invention as defined above may be obtained using standard procedures well known in the art, for example by reacting a sufficiently basic compound, for example an alkyl amine with a suitable acid, for example, hydrochloride or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-I-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like.

As used herein, the term "compounds or pharmaceutically acceptable salts" include hydrates and solvates thereof.

Medical Use

The route of administration of pharmaceutical compositions of the present invention may be oral, parenteral, buccal, vaginal, rectal, inhalation, insufflation, sublingual, intramuscularly, subcutaneous, topical, intranasal, intraperitoneal, intravenous, epidural, intrathecal, intracerebroventricular and by injection into the joints.

Preferably, the route of administration of the pharmaceutical compositions of the present invention is oral or parenteral. More preferably, the route of administration of the pharmaceutical compositions of the present invention is parenteral.

The parenteral route of administration of the pharmaceutical compositions of the present invention may be subcutaneous or intravenous. Preferably, the parenteral route of administration of the pharmaceutical compositions of the present invention is subcutaneous.

The frequency and optimum dosage of administration of the present invention will depend on the particular condition being treated and its severity; the age, sex, size and weight, and general physical condition of the particular patient; other medication the patient may be taking; the route of administration; the formulation; and various other factors known to physicians and others skilled in the art. For example, the frequency of administration will vary for the disease being treated from once weekly to once monthly. Preferably, the frequency of administration is every 7 to 31 days. Depending on the dose, the frequency of administration may be once every 7 to 10 days, or very 7 to 14, or 21 or 31 days. More preferably, the frequency of administration is every 2, 3 or 4 weeks. Yet more preferably, the frequency of administration is every 2 weeks. Most preferably, the frequency of the administration is every 4 weeks or calendar month. The quantity of methotrexate to be administered will vary for the patient being treated and will vary from about 5 to 100 mg per dosing. The quantity of methotrexate to be administered may vary from about 60 ng/kg of body weight to about 0.4 mg/kg of body weight per dosing. For instance, dosages can be readily ascertained by those skilled in the art from this disclosure and the knowledge in the art. Thus, the skilled artisan can readily determine the amount of compound and optional additives, vehicles, and/or carrier in compositions to be administered in methods and uses of the invention. For example, in the treatment of rheumatoid arthritis, the optimum dosage level and frequency have been found to be a once weekly or once every 5 to 12 days administration of methotrexate, with 15 mg/week as the starting dose and a subsequent 5 mg dose increase every month until either a dose level of 30 mg/week or MTD is reached. In psoriasis vulgaris it was found, that a starting dose of 17.5 mg/week and a dose increase of 5 mg after eight weeks resulted in optimum control of disease in methotrexate responders. Preferably, the effective methotrexate dosage of the present invention in the treatment of autoimmune disease, e.g. RA and/or psoriasis will be below 20 mg per dosing interval. More preferably, the effective methotrexate dosage of the present invention in the treatment of autoimmune disease, e.g. RA and/or psoriasis will be below 18 mg per dosing interval. Most preferably, the effective methotrexate dosage of the present invention in the treatment of autoimmune disease, e.g. RA and/or psoriasis will be below 15 mg per dosing interval.

Pharmaceutical Compositions

The combination of the invention may be used on its own but will generally be administered in the form of a pharmaceutical composition in which methotrexate and novobiocin are in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

For preparing pharmaceutical compositions of the invention, inert, pharmaceutically acceptable carriers can be either solid or liquid. A solid carrier can be one or more substances, which may also act as diluent, flavoring agent, solubilizer, lubricant, suspending agent, binder, or tablet disintegrating agent; it can also be an encapsulating material. A liquid carrier can be one or more substances, which may act as solubilizer, suspending agent, or stabilizer.

Solid form compositions include powders, tablets, dispersible granules, capsules, cachets, and suppositories. Liquid forms include parenteral forms (intravenous, subcutaneous or intra-muscular administration), syrups, and soft gelatin capsules (SGCs).

Depending on the mode of administration, the pharmaceutical composition may comprise from 0.05 to 99% wt, or from 0.5 to 90% wt, or from 0.75 to 25% wt, or from 1 to 10% wt therapeutically active ingredients, all percentages by weight being based on total pharmaceutical composition.

Parenteral Solution and Administration Devices for Subcutaneous Administration

Parenteral devices for the subcutaneous administration of methotrexate in a liquid vehicle or carrier (e.g. prefilled syringes, ampoules, carpoules or prefilled autoinjector) have been widely used in the treatment of autoimmune diseases, including rheumatoid arthritis, psoriasis, psoriatic arthritis and Crohn's disease. The currently marketed parenteral solution (concentration levels available vary from 10 mg/mL to 50 mg/mL) have the advantage over the currently marketed tablets that they display a more linear and less variable pharmacokinetic in patients. This is especially advantageous at dosage levels >15 mg/administration as the systemic methotrexate exposure levels hardly increase when the patient is administered oral dosages above 15 mg, while the systemic methotrexate exposure levels increase linearly when the patient is administered dosages above 15 mg per the subcutaneous administration route. The pharmaceutical compositions of methotrexate are typically isotonic, aqueous solutions with a pH of 7.5 to 9. Isotonization agents used include pharmaceutically acceptable salts (e.g. sodium chloride, potassium chloride), sugars (e.g. glucose, lactose), sugar alcohols (e.g. mannitol, sorbitol) and combinations hereof. Other pharmaceutically acceptable excipients that may be used in a pharmaceutical composition of the invention are pH controlling agents (e.g. acetate-, phosphate- or citrate buffers), antioxidants (e.g. ascorbic acid, acetyl cysteine, sulfurous acid salts like bisulfite or metabisulfite), antimicrobial agents (e.g. phenol, parabens, meta-cresol, benzyl alcohol), solubilizers, co-solvents (e.g. cyclodextrines, povidone, polysorbate, lecithin, glycocholate), viscosity controlling agents or a combination thereof.

Composition

A. Liquid Matrix
  a. methotrexate or a pharmaceutically acceptable salt thereof;
  b. novobiocin or a pharmaceutically acceptable salt thereof;
  c. excipients, i.e. pharmaceutically acceptable carrier materials that are considered safe and may be administered to an individual without causing pharmacological (adverse) events or interactions, including, but not limited to, solvents, preservation agents, pH adjusting agents, solubilizers, co-solvents and combinations thereof.
    a. solvent; exemplary solvents include sterile water for injection USP 10% to 80% by weight and water being present in an amount from about 1% up to 100% by weight.
    b. isotonization agent; exemplary agents include sodium chloride or potassium chloride
    c. ionization agent; exemplary agents include sodium hydroxide B. Glass Container (Type I Glass)
  a. carpoule
  b. ampoule
  c. syringe C. Medical Device
  a. autoinjector Production Process A. Liquid Matrix The liquid matrix is prepared by mixing methotrexate, or a pharmaceutically acceptable salt thereof, with novobiocin, or a pharmaceutically acceptable salt thereof with the excipients, such as solvents (i.e. sterile water for injection USP) and solubilizing agent (e.g. sodium hydroxide) and isotonization agent (e.g. sodium chloride). The therapeutically active agent is present in an amount from about 1% to about 50% by weight. The ionizing agent is present in an amount from about 0 to 2.2 mole per mole of the therapeutically active agent. Water is present in an amount from about 10% to about 98% by weight. Isotonization agent is present in an amount from 0% to about 1%. The pH of the resulting liquid matrix is typically about 7.5 to 9.

B. Filling of Ppharmaceutical Device

The liquid matrix is filtered over 0.22 um sterile filters into Type I glass containers (carpoule, ampoule, syringe). The carpoule or syringe is optionally placed into an aut injector.

Soft Gelatin Capsules

Filled one-piece soft gelatin capsules (SGCs) have been widely used for years to encapsulate pharmaceuticals in a liquid vehicle or carrier. Liquid vehicles can be either hydrophilic or lipophilic. Hydrophilic vehicles include polyethylene glycols (PEGs), polyoxyethylene-polyoxypropylene copolymers (poloxamers), propylene glycol (PG), glycerin, low molecular weight alcohol or water. Lipophilic vehicles include free fatty acids and fatty acid esters of hydroxyl compounds (e.g. ethanol, propylene glycol, sorbitol, PEGs). The fatty acid composition of such esters can be short chain (SC, <8 carbon atoms), medium chain (MC, 8-10 carbon atoms) or long chain (LC, >12 carbon atoms). For example, a mixture of a LC triglyceride, e.g. vegetable oil and a MC triglyceride, e.g. fractionated coconut oil.

Hydrophilic liquid vehicles usually contain less than about 20% water by weight, because the water tends to dissolve the gelatin shell of the SGC. Other solvents such as propylene glycol, glycerin, low molecular weight alcohols, ketones, acids, amines, and esters also tend to degrade or dissolve the gelatin shell to some extent if present in higher percentages by weight. SGCs are further sensitive to pH: highly acidic liquids may hydrolyze the gelatin, resulting in leaks, while basic liquids may tan the gelatin, resulting in decreased solubility of the gelatin shell. The pH in the encapsulated liquid may range from about 2.5 to about 7.5. The polyethylene glycols (PEG) are susceptible to ester formation with acids. Addition of organic acids helps to prevent ester formation between the pharmaceutical ingredients and the PEGs in the capsule. Pharmaceutical liquids are usually enclosed in SGCs as either viscous solutions or suspensions. Solutions provide the best liquid form for obtaining optimal "content uniformity" in a batch. In addition, solutions typically provide a faster and more uniform absorption of pharmaceuticals as compared to pharmaceutical compositions containing non- or partly-dissolved active ingredients (e.g. suspensions, tablets).

Composition

A. Liquid Matrix
  a. methotrexate or a pharmaceutically acceptable salt thereof;
  b. novobiocin or a pharmaceutically acceptable salt thereof;
  c. excipients, i.e. pharmaceutically acceptable carrier materials that are considered safe and may be administered to an individual without causing pharmacological (adverse) events or interactions, including, but not limited to, bulk filling agents, solvents, plasticizers, wetting agents, surfactants, preservation agents, flavors, opaqifiers, dyes, pH adjusting agents, crystallization inhibitors and combinations thereof.
    a. solvent; exemplary solvents include polyethylene glycols with a molecular weight ranging from 200 to 1500, poloxamers, propylene glycol, glycerin, low molecular weight alcohols (e.g. ethanol) and water.

In a preferred aspect, a mixture of PEG400 and/or PEG 600 and water is used as the solvent, with PEGs being present in an amount from about 10% to 80% by weight and water being present in an amount from about 1% to 18% by weight.

b. Solubility enhancers; exemplary solubility enhancers include ionizing agents (by causing partial ionization or neutralization), polyvinylpyrrolidinone (PVP), and polysorbates. Ionizing agents include both hydroxide—and hydrogen ion species; exemplary hydroxide ion species, including but not limited to metal hydroxides (e.g. NaOH, KOH, $NH_4OH$, $Ca(OH)_2$, $Al(OH)_3$ and $Mg(OH)_2$) and hydrogen ion species, including but not limited to HCl, HBr, HI, H2SO4, acetic acid, butanoic acid, citric acid, fumaric acid, maleic acid, malic acid, lactic acid, propionic acid, pyruvic acid, and sulfonates (e.g. methane-, ethane- or benzene sulfonates). The ionizing agent is present in an amount between 0.2 and 2.4 mole equivalents per combined mole equivalent of methotrexate and novobiocin. Ionizing agents may also be used to adjust the pH of the liquid matrix. Preferably, the pH of the liquid matrix is 2.5 to 7.5.

B. Capsule Shell
a. Gelatin of either Type A or Type B;
b. Other, including
    a. plasticizers, to make the gelatin material softer and more flexible; exemplary plasticizers include glycerin, sorbitol solutions (i.e. mixtures of sorbitol and sorbitan), and other polyhydric alcohols such as propylene glycol, maltitol or combinations thereof.
    b. opacifiers, to protect the active ingredient from light; exemplary opacifiers include titanium dioxide, zinc oxide, or calcium carbonate or combinations thereof.
    c. colorants, used for product identification and differentiation purposes include pharmaceutically acceptable synthetic and natural dyes
    d. humectants, to suppress/control the water activity of the SGC; exemplary humectants include glycerin and sorbitol
    e. preservatives, to suppress investation from for example molds and yeasts; exemplary preservatives include alkyl esters of p-OH-benzoic acid (i.e. parabens)
    f. flavorings, in the presence of buffering salts and acids; used to mask unpleasant taste or odor of the liquid matrix, pharmaceutically acceptable synthetic and natural flavors can be used in conjunction with buffering salts and acids to prohibit cross-linking of the gelatin due to aldehydes present in the flavoring agent(s).

Production Process
A. Liquid Matrix

The liquid matrix is prepared by mixing methotrexate, or a pharmaceutically acceptable salt thereof, with novobiocin, or a pharmaceutically acceptable salt thereof with the excipients, such as solvents (e.g. water, PEGs, and propylene glycol) and solubilizing agents (e.g. ionizing agent(s), and PVP) at a temperature of 50° C. to 70° C. The resulting solution is encapsulated using the appropriate gel mass. The pharmaceutical agents are present in an amount from about 0.5% to about 50% by weight. The deionizing agent is present in an amount from about 0.2 to 2.5 mole per mole of the therapeutically active pharmaceutical agent. Water is present in an amount from about 0% to about 20% by weight and polyethylene glycol is present in amount from about 10% to about 80% by weight. Optionally, propylene glycol and/or PVP are present in an amount from about 1% to about 10%.

B. Gel Mass

The main ingredients of the SGC shell are gelatin, plasticizer, and purified water. Typical gel formulations contain (w/w) 40-50% gelatin, 20-30% plasticizer, and 30-40% purified water. Most of the water is subsequently lost during capsule drying. The ingredients are combined to form a molten gelatin mass using either a cold melt (i.e. mixing gelatin with plasticizer (typically at ambient temperature of 18-22° C.) and chilled water and then transferring the mixture to a jacket-heated tank, followed by heating under vacuum at 57-95° C. for 15-30 minutes to a homogeneous, deaerated gel mass. Additional shell additives can be added to the gel mass at any point during the gel manufacturing process or they may be incorporated into the finished gel mass using a high torque mixer) or a hot melt (i.e. mixing the gelatin to a warm mixture of plasticizer and water (60-80° C.) and stirring until complete melting of the gelatin is achieved) process. The prepared gel masses are transferred to preheated, temperature-controlled, jacketed holding tanks where the gel mass is aged at 50-60° C. until used for encapsulation.

C. Soft Gelatin Capsule

The manufacturing process used to produce SGCs is typically the rotary die encapsulation process. The molten gel mass (48-65° C.) is fed at from a reservoir onto two separate rotating cool casting drums to form two spaced flat sheets/ribbons of gelatin in a semi-molten state. The ribbons are extracted from the cooling drums and fed around rollers that lubricate them with food-grade lubricant oil (typically fractionated coconut oil or soybean oil). In a preferred aspect, the SGCs display printing on the surface for identification of the pharmaceutical composition. The liquid matrix to be encapsulated is fed into a positive displacement pump, and injected from a wedge into the space between the gelatin ribbons as they meet on the rim of the opposing die cavities, right after the lower seam of the SGC is being formed. The production of the SGC is completed by sealing the SGC halves together (formation of the upper seam) by application of heat and pressure. The finished SGCs are ejected by continuous rotation of the dies, carried on a conveyer into a tumble dryer.

EXAMPLES

The following, non-limiting examples illustrate pharmaceutical compositions of the invention for either oral or parenteral administration.

Example 1

In the following example, the liquid matrix is prepared by mixing methotrexate (therapeutic amount), novobiocin (non-therapeutic amount) with a solubilizing agent (water and polyethylene glycol) and other excipients at a temperature of 50° C. to 70° C. The resulting solution is encapsulated in a soft gelatin capsule using the appropriate gel mass.

TABLE 1

Liquid matrix composition of examples 1A-1I

| Ingredients % (by weight) | A | B | C | D | E | F | G | H | I |
|---|---|---|---|---|---|---|---|---|---|
| Methotrexate sodium | 1 | 1.5 | 3 | 3 | 3.5 | 3.5 | 3.5 | 3.5 | 3.5 |
| Novobiocin sodium | 27.5 | 20 | 20 | 15 | 7.5 | 5 | 4.5 | 3 | 2.5 |
| PVP | 2 | 1.75 |  | 2 | 1.75 | 1.5 | 1.5 | 1.5 | 2 |
| PG | 2 |  | 2 |  | 1 | 0.5 |  | 0.5 |  |
| Lactic acid | 2.5 | 1.75 | 2 | 1 | 1 | 0.5 | 0.5 | 1 | 0.5 |
| PEG400 | 34 | 45 | 20 | 60 | 39 |  | 78 | 28 | 19 |
| PEG600 | 22 | 22 | 45 | 12 | 39 |  | 51 | 65 | 78 |
| Water | 9 | 8 | 8 | 7 | 7.25 | 11 | 10.5 | 6.5 | 13.5 |

Example 2

In the following example, the liquid matrix is prepared by mixing methotrexate (therapeutic amount), novobiocin (non-therapeutic amount) and other excipients with water suitable for injection (USP). The resulting matrix is filtered accordingly to ensure sterility and transferred to the appropriate glass container (e.g. syringe, carpoule or ampoule)

TABLE 2

Liquid matrix composition of examples 2A-2I

| Ingredients % (by weight) | A | B | C | D | E | F | G | H | I |
|---|---|---|---|---|---|---|---|---|---|
| Methotrexate | 5 | 2.5 | 1.25 | 4 | 2.5 | 2.85 | 2.4 | 1.9 | 1 |
| Novobiocin | 7.5 | 7 | 8 | 8 | 5 | 3.85 | 8.1 | 2.6 | 6.5 |
| NaOH | 1.1 | 0.7 | 0.7 | 1.1 | 0.6 | 0.85 | 0.7 | 0.55 | 0.3 |
| NaCl | 0.4 | 0.4 | 0.4 | 0.4 | 0.4 | 0.4 | 0.4 | 0.4 | 0.4 |
| Water | 86 | 83.1 | 89.65 | 86.5 | 91.5 | 92.05 | 88.4 | 94.55 | 91.8 |

TABLE 3

Liquid matrix composition of examples 2J-2R

| Ingredients % (by weight) | J | KB | LC | M | NE | OF | PG | QH | IR |
|---|---|---|---|---|---|---|---|---|---|
| Methotrexate natrium | 5.2 | 2.6 | 1.3 | 4.1 | 5.2 | 3.1 | 3.1 | 2.6 | 2.6 |
| Novobiocin natrium | 7.7 | 7.1 | 8.3 | 8.3 | 11.6 | 11.8 | 5.9 | 16.4 | 6.5 |
| NaCl | 0.4 | 0.4 | 0.4 | 0.4 | 0.4 | 0.4 | 0.4 | 0.4 | 0.4 |
| Water | 83.7 | 89.3 | 90 | 83.6 | 82.8 | 84.7 | 90.6 | 80.6 | 90.5 |

The advantages of administration to a patient in need of treatment of a pharmaceutical composition of the invention, containing a combination of a therapeutically effective amount of 5 to 100 mg of methotrexate and a therapeutically inactive amount of 5 to 300 mg of novobiocin per dosing interval, preferably 5 to 30 mg of methotrexate and 5 to 100 mg novobiocin per dosing interval, most preferably 7.5 to 20 mg of methotrexate and 5 to 75 mg novobiocin per dosing interval at a once weekly to once monthly treatment interval, preferably every 7, 10, 14, 21 or 28 days, most preferably every 14 or 28 days, versus the administration of existing methotrexate treatment regimes in disease (e.g. auto immune diseases, for example rheumatoid arthritis), can be demonstrated both in healthy controls/patients, as well as in in vitro models (for example in cell assay models), in ex vivo models (for example in tissue assay models) and/or in in vivo (i.e. animal models). Such models enable the study of both the pharmacodynamic, pharmacokinetic and pharmaco-toxic effects of the treatments in disease, specifically auto immune disease of a chronic nature, including diseases like rheumatoid arthritis or psoriasis or Crohn's disease. Corresponding animal models for rheumatoid arthritis for example include, but are not limited to, the collagen-induced arthritis model (CIA), the pristane-induced arthritis model (PIA), or the adjuvant-induced arthritis model (AIA). Corresponding general in vitro/ex vivo models include, but are not limited to, cell apoptosis models (e.g. neutrophil apoptosis) or quantification of (anti-)-inflammatory/matrix destructing agents (e.g. quantification of mRNA levels of MMP1 and MMP3). Corresponding MTX-specific in vitro models that demonstrate the advantage of the invention include, but are not limited to, cell assays that quantify the levels of intracellular polyglutamated derivatives of MTX. It has been shown, that the side effects seen with the current methotrexate treatment regimes in patients also occur in healthy rodents, including hemotoxic, gastrointestinal and hepatoxic effects. Comparable to the situation in human chronic disease, the pharmacokinetics and/or pharmacodynamics and/or pharmacotoxicity of administered doses in animal models with chronic disease, specifically animal models with rheumatoid arthritis, may be different. The combined, simultaneous study of the pharmacodynamic, -kinetic and -toxicologic effects in chronic animal models of auto immune disease enables the evaluation of the risk-benefit balance in the patient situation, without jeopardizing patient safety. Thus, it is preferred to study not only the pharmacodynamic and pharmacokinetic effects of the product or composition of the invention in such animal models but, where feasible, to also include the safety and toxicological effects of the treatment of the invention, and optionally compare the results to the current methotrexate treatment regimes. In animal models of autoimmune disease, for example the pristane-induced arthritis (PIA) rat model of RA, treatment with a pharmaceutical composition of the invention, containing a combination of the invention comprising or consisting of a therapeutically effective amount of methotrexate and a therapeutically inactive amount of novobiocin per dosing interval, is believed to result in:

- an improved or comparable therapeutic effect of methotrexate in disease, particularly in autoimmune disease, including rheumatoid arthritis (RA), psoriasis (Pso), psoriatic arthritis (PSA), and Crohn's disease (CD), versus treatment with, respectively, a similar or lower dose of current methotrexate treatments; and/or
- a comparable therapeutic effect of methotrexate in disease, particularly in autoimmune disease, including RA, Pso, PSA, CD, with a reduced administration rate versus available methotrexate treatments; and/or
- an increased tolerability to methotrexate, i.e. a reduced rate and/or severity of adverse events, including hepatic, gastro-intestinal or haematological adverse events, versus currently available methotrexate treatments; and/or an improved compliance to disease treatment, particularly autoimmune disease treatment, including diseases like RA, Pso, PSA, and CD, versus current methotrexate treatments; and/or an increased oral bioavailability of methotrexate in disease, particularly in autoimmune disease, including RA, Pso, PSA, and CD, versus available methotrexate treatments; and/or a decreased rate in methotrexate treatment abandoning/change to treatments with higher cost and/or side effects in disease, particularly in autoimmune disease, including RA, Pso, PSA, and CD, versus currently available methotrexate treatments.

The following non-limiting examples illustrate the efficacy and safety of the invention.

Example 3

Induction of Neutrophil Apoptosis (In Vitro/Ex Vivo Model of Arthritis) to Eestablish the Pharmacodynamic Eeffects of Novobiocin Apoptosis, in contrast to necrosis, is the demise of a cell through a series of controlled sequential events, resulting in an increase of anti-inflammatory mediators instead of invoking an inflammatory response, because the contents of the cell are removed by phagocytosis and not released to the direct environment. Apoptosis involves the activation of caspases, including caspase 3. Aberration in expression and/or function of the regulators of cell death through apoptosis is thought to result in pathological conditions, including autoimmune diseases and cancer. Although apoptotic cells are uncommonly observed in vivo in RA tissues, in vitro inflammatory cells from RA tissues, like synoviocytes, T-cells and macrophages, are highly susceptible to apoptosis induced through the FAS-TNF-receptor pathway. The absence of apoptotic cells in vivo may be explained by the high levels of nitric oxide in RA tissues, which inhibits caspase 3 and thus cell apoptosis.

In patients with early stage RA, before any treatment and 4 months after reaching a therapeutic dose of MTX of more than 20 mg/week of MTX, neutrophil apoptosis was delayed within 6 h and 22 h, as measured by the loss of DNA content. This was observed in patients without any pre-treatment, while a restoration of neutrophil apoptosis to healthy control levels was observed in patients with MTX treatment (Weinman P et al. 2007).

Calcium pyrophosphate dihydrate (CPPD) crystals are found in the synovial joints of patients and has been shown to correlate to the large numbers of neutrophils—and other immune cells—and their survival. Tudan et al. (1997) showed that both topoisomerase I and II inhibitors counteract CPPD-triggered prolonged survival of neutrophils. Novobiocin is a topoisomerase II inhibitor and at therapeutically relevant concentration levels, is expected to counteract CPPD-triggered prolonged survival of neutrophils. Such a pharmacodynamic effect of Novobiocin may be quantified either through activity (levels) of caspase 3, an apoptotic cleavage enzyme, or cytoplasmic histone-associated-DNA fragmentation assessment, using commercially available kits.

Neutrophils may be obtained either from patients/disease model animals (e.g. CIA or PIA rat model), demonstrating ex vivo the in vivo treatment effects on their survival, or, alternatively, from healthy control individuals/animals. In the latter model, the effect on neutrophil apoptosis can be either studied directly, or indirectly, exposing the cells in vitro to a challenge that prolongs their survival (e.g. CPPD crystals).

Methods:

CPPD ($Ca_2P_2O_7.2H_2O$; triclinic form) crystals can be obtained using well described methods (Burt H M et al. 1989; Gras P. et al. 2013). Plasma protein coating of the crystals is achieved through incubation of the crystals in 50% plasma (Tudan C et al. 2003). The CPPD crystals are used in experiments with neutrophils from healthy control individuals/animals to mimic arthritic disease.

Neutrophils are separated from fresh human (healthy control/patient) or rat (healthy control; disease model) blood using standard methods and suspended in buffer at a concentration of $1 \times 10^6$ cells/ml. The cells are incubated at 37° C. with occasional tumbling.

Stock solutions of TNFalpha, Methotrexate and Novobiocin are prepared in DMSO, keeping the DMSO concentrations in the cell suspensions below 0.1% during the experiment. The apoptosis rate following the administration of vehicle without active agent (negative control) represents the baseline rate of apoptosis (no effect level), while the apoptosis rate following the administration of TNFalpha (positive control) represents the maximum rate of apoptosis (100% effect level).

Results:

No pharmacodynamic effects of novobiocin are observed in neutrophils obtained from patients with rheumatoid arthritis or in neutrophils obtained from one of the corresponding disease model animals (PIA rat) in concentrations <60 uM;

No pharmacodynamic effects of novobiocin are observed in neutrophils obtained from healthy subjects or rat in concentrations <60 uM;

No pharmacodynamic effects of novobiocin on CPPD-induce prolonged survival are observed in neutrophils obtained from healthy subjects or rat in concentrations <60 uM;

Neutrophils from healthy controls (human/rat); effect of NOV on CPPD-induced prolonged survival (control =base line; TNFalpha is 100% effect): No pharmacodynamic effects of novobiocin are observed in neutrophils in concentrations <50 uM.

Example 4

Effect of MTX and NOV on IL-1 Induced Overexpression of Metalloproteinases 1 (Collagenase) and 3 (Stromelycin)

Progressive cartilage degradation and consequent bone erosion and joint deformity, as seen in arthritis, is amplified by the increased levels of pro-inflammatory agents. One of the key role players is interleukin 1 (IL-1), inducing altered expression levels of the mRNA of metalloproteinases (MMPs) and tissue inhibitors of metalloproteinases (TIMPs). For example, IL-1 causes overexpression of mRNA of MMP1 (collagenase) and MMP3 (stromelysin1), leading to increased synthesis and release of these matrix protein degrading agents from articular chondrocytes. Martel-Pelletier J et al. (1991) reported the effect of IL-1 on cartilage degradation using in vitro models of human cartilage and culture chondrocytes, showing increased synthesis levels of MMP1 and MMP3. Nose M. et al. (1997) showed that the DMARDs Sulfasalazin (SSZ) and Methotrexate (MTX) both suppressed the IL-1 induced increase in MMP1 expression. SSZ also suppressed the IL-1 induced increase in MMP3 expression. Jackson J K et al. (2008) showed that at 1×10$^{-7}$ M, the topoisomerase I inhibitors Camptothecin almost completely inhibited the IL-1 induced increase in MMP1 and MMP3 mRNA expression, while other topoisomerase I and II inhibitors were able to counteract the IL-1 effects at concentration levels of 1×10$^{-5}$ M. At these higher concentration levels, however, the normal physiology of the chondrocytes is compromised as shown by inhibition of the expression of proteoglycan, a protein that is a major component of the animal extracellular matrix. For example, cartilage tissue is a combination of proteoglycan and collagen.

The anti-inflammatory effect on IL-1 induced cartilage degradation can be studied in vitro either in chondrocytes isolated from cartilage from humans/patients or from animals (healthy controls/disease models) and have been extensively described in the literature (for example in a review from Oteo et al. 2005).

Methods:

Primary chondrocyte culture was freshly isolated from calf cartilage. The cells were plated (at 2.5×10$^6$ per mL) in 100×20 mm culture dishes and incubated in Ham's F12 medium containing 5% fetal bovine serum (FBS) overnight at 37° C. The cells were starved with serum-free medium overnight. The cells were pretreated with MTX, NOV or a combination of MTX with 1, 2, 10 or 20 eq of NOV for 6 hours. Then IL-1 (20 ng/mL) was added to each plate and the plates were incubated for an additional 18 h.

Total RNA was isolated by the acidified guanidine isothiocyanate method and subjected to electrophoresis on a denatured gel. Denatured RNA samples were analyzed by gel electrophoresis in a 1% denaturing gel, transferred to a nylon membrane and hybridized respectively with the $^{32}$P-cDNA probes for MMP1, MMP3 and proteoglycan and analyzed.

Results

No pharmacodynamic effects of novobiocin are observed on the IL-1 induced mRNA upregulation of both MMP1 and MMP3 in concentrations <100 uM.

No additional pharmacodynamic effects of novobiocin are observed on the inhibition of the IL-1 induced mRNA upregulation of MMP1 by MTX in concentrations <100 uM.

Example 5

Effect of NOV on Intracellular Polyglutamation Levels/Rate of MTX

A crucial property of MTX is its susceptibility to polyglutamation by the same enzymes that polyglutamylate physiological folates. Folyl polyglutamate synthetase (FPGS) catalyses the condensation of successive glutamate residues to the γ-carboxyl group of MTX, a mono-glutamate (Glue), to yield MTX-Glu$_{2-7}$ derivatives. The number of glutamate residues is positively correlated to the probability of clinical success in the treatment of autoimmune disease like rheumatoid arthritis (Stamp L et al. 2011).

In vitro studies have shown that the conversion and accumulation of MTX into MTXPGs is a function of both the concentration of extracellular MTX and of the duration of the exposure to MTX.

Several cell types can be used to study the polyglutamation of MTX. For example, fibroblasts, red blood cells and myeloid precursor cells have been used to determine rate and extent of polyglutamation. As the rate of polyglutamiation of methotrexate may be different between normal (resting) cell populations versus inflammatory (activated) cell populations, in vitro studies with cell populations that can be easily obtained and cultured are of special interest. For example, peripheral blood mononuclear cells (PBMCs) obtained from healthy human volunteers/control animals and patients with auto-immune disease/disease model animals can be used to study the effect of treatment with a combination of the invention of a therapeutically effective amount of methotrexate and a therapeutically ineffective amount of novobiocin versus a therapeutically effective amount of methotrexate alone. PBMCs include lymphocytes (45-70% CD3+ T cells, up to 15% B cells and up to 15% NK cells), monocytes (10-30%) and dendritic cells (1-2%).

Methods:

In addition to human-derived PBMCs, the effects can be studied using for example rat-derived PBMCs from healthy control animals and disease model animals. Routine techniques for the isolation of PBMCs include density centrifugation with Ficoll-Paque and isolation by cell preparation tubes (CPTs) and SepMate tubes with Lymphoprep. PBMCs can be incubated in RPMI-1640 medium with 10% FBS and 1% penicillin/streptomycin/glutamine in microtiter plates—for example 4×10$^5$ cells in 200 uL—at 37° C. in 5% CO$_2$ for several days. Supernatants and cells can be kept frozen at −80° C. until analysis. Concentrations of methotrexate and methotrexate polyglutamates, can be determined with use of LC-MS/MS techniques.

Results:

The quantities of MTX-Glu$_{2-7}$ derivatives observed following incubation of PBMCs with a combination of treatment equivalent dose levels of methotrexate and novobiocin (1, 2, 10 or 20 equivalents to methotrexate) significantly exceeded the quantities of MTX-Glu$_{2-7}$ derivatives following incubation with methotrexate alone.

Example 6

Pharmacodynamics (Efficacy and Safety) of an Immediate Release Formulation of the Combination of Methotrexate and Novobiocin Versus Immediate Release Formulations of Methotrexate or Novobiocin Alone in Rheumatoid Arthritis Following Parenteral and/or Oral Administration Method PIA rat model—in accordance with local (Malmo, Sweden) animal ethic license number M82-15: DA rats (females, 8-10 weeks; Envigo Europe) are kept at 12 h light/dark cycles, in polystyrene cages (type IIIH cages, 2-3 rats per cage) containing wood shavings and fed standard rodent chow and water ad libitum. The animals are acclimatized for approximately one week before initiation of experiment. All rats are weighed day 0, the day of disease induction, for determination of mean weight of the rats included in the experiment. Arthritis is induced by subcutaneous (s.c.) administration of 200 µl pristane on Day 0. The rats are anesthetized by inhaling a mixture of Isoba vet (3.5%) and oxygen. The root of the tail is cleaned with 70% ethanol and the oil is injected approximately 0.5 cm from the root of the tail. A slight pressure is put on the injection site for 5 seconds after injection to prevent leakage of the oil. Test compounds are administered either i.v. or p.o. (by gavage). Disease is evaluated three times per week from disease onset using a macroscopic scoring system of the four limbs ranging from 0 to 15 (1 point for each swollen or red toe, 1 point for a swollen or red mid foot digit or knuckle, 5 points for a swollen ankle) resulting in a maximum total score of 60 for each rat. The disease scoring is done in a double-blind fashion, i.e. the scorer is unaware of the treatment received by the animal. Blood is collected from the sublingual vein in Li-Heparin containing tubes at different time points after administration of test compounds, and used to determine pharmacokinetic (e.g. Tmax, Cmax, AUC), pharmocodynamic (e.g. cytokine/chemokine markers of inflammation, number of different blood cell types) and pharmacotoxicologic parameters (e.g. liver and/or kidney markers, incl. AST, ALT, CK).

Results:

Daily, per oral administration of up to 80 mg/kg* of novobiocin from day 11 to 21 (i.e. after onset of disease) had no therapeutic effect on the pristane-induced arthritis, while, for example, administration of 0.1 mg/kg of methotrexate every third day from day 7 (i.v.) completely ameliorated the inflammatory effects of pristane.

*po admin of 55 mg/kg novobiocin to healthy animals results in an average $C_{max}$ of 23.3 mg/L and an average $AUC_{24h}$ of 109.8 mg*h/L.

Example 7

Model for Assessing Pharmacokinetics of the Administration of a Combination of Methotrexate and Novobiocin Versus Methotrexate Alone Following Parenteral and/or Oral Administration List of Abbreviations AUCinf.: Area under the curve to infinity; AUClast.: Area under the curve to the last data point; Cmax: maximum concentration; F: bioavailability; i.v.: intra venous, i.p.: intra peritoneal, LC: liquid chromatography; MS: mass spectrometry; NCA: non-compartmental analysis; PBS: phosphate buffered saline; PK: pharmacokinetic; p.o: per os/per oral; MTX: methotrexate; NOV: novobiocin; TI: Test Item; Tmax: Time of maximum concentration; $T_{1/2}$: half life In vivo study protocol—in accordance with local (Malmo, Sweden) animal ethic license number M388-12: Following acclimatization to the housing conditions for a minimum of 7 days after arrival, male Wistar (Hannover) rats (Taconic, Denmark), average weight 300 g; average age 8-10 weeks, are treated with test items (see table 1); 12-16 h prior to dosing all food except for an amount equivalent to a half day consumption is removed. The test items are administrated using a soft gavage tube (p.o.) or by injecting the test item in the tail vein (i.v.). The volume given is 5 mL/kg (p.o.) or 1 mL/kg (i.v.). Before i.v administration rats are anesthetized using isoflurane. The rats are conscious during sample collection and the blood is taken from the sub-lingual vein. Blood samples are collected from each rat over a period of up to 24 h. At each time point two aliquots of 50 µL each is added to a vial containing 150 µL of sterile water. The samples are mixed immediately and stored at −18° C. until preparation for bioanalysis is commenced. All formulations are prepared on the same day that dosing takes place. The body weight of the rat is recorded before dosing. The weight of the syringe is recorded before and after administration to allow calculation of the actual amount of test sample delivered. The actual doses are used during the evaluation of the data.

TABLE 4

Study Design (3-5 animals per dosage group)

| Route | Dose MTX | Dose NOV | Vehicle |
|---|---|---|---|
| ip | 0.2 to 5.0 mg/kg | 0.1 to 20 eq of the MTX dose | PBS |
| ip | 0.2 to 5.0 mg/kg | none | PBS |

TABLE 4-continued

Study Design (3-5 animals per dosage group)

| Route | Dose MTX | Dose NOV | Vehicle |
|---|---|---|---|
| po | 0.5 to 10.0 mg/kg | 0.5 to 20 eq of the MTX dose | PBS |
| po | 0.5 to 10.0 mg/kg | none | PBS |

Bioanalysis:

The plasma levels of methotrexate and novobiocin are determined using LC-MS/MS in mrm (multiple reaction monitoring) mode. Samples and standards are injected by a HTC PAL from CTC analytics into an LC system from Shimadzu consisting of a high-pressure gradient system of two LC-10 AD pumps controlled by a SCL-10A controller from Shimadzu. The samples are separated using reverse-phase chromatography with gradient elution at a flow rate of 0.8 mL/min. Mobile phases are A:94.9/5/0.1 water/acetonitrile/formic acid and B:5/94.9/0.1 water/acetonitrile/formic acid. Gradient starts at 0% B and increases linearly to 100% B in 4 minutes, 100% B is kept for 0.5 minutes and then the system returns to 0% B in 0.1 minutes. The system is equilibrated for 1.4 minutes until the total run time of 6 minutes. The eluent is analysed by a Quattro Ultima from Micromass equipped with an electrospray ion source. Data are collected, and calibrations are calculated by MassLynx 4.0 software. Methotrexate and novobiocin are separated on a Waters Symmetry C18 50×2.1 column. The eluent is ionized by negative ion electrospray.

The diluted blood sample (50 µL blood, 150 µL water) is thawed and mixed with 400 µL of acetonitrile, to precipitate the protein. The sample is centrifuged at 5000 g for 5 minutes and 100 µL of the supernatant is transferred to a 300 µL glass vial and 100 µL of water is added to reduce the acetonitrile concentration.

Positive and negative mode MS/MS are employed for methotrexate and novobiocin. The concentration of the standard curve is in the range from 5 nM to 15625 nM. Samples with analyte concentrations above the upper limit of quantification are diluted with matrix to reach within the assay range. A non-compartmental analysis (NCA) is performed using the Phoenix WinNonLin analysis tool.

Results:

The pharmacokinetics of novobiocin are linear both following oral (gavage) and parenteral (ip) administration within the applied dose ranges.

TABLE 5

The effect of 20 mol. equivalents of novobiocin on the pharmacokinetic parameters of methotrexate (2 mg/kg) following oral co-administration (gavage).

| Treatment | $C_{max}$ MTX nmol/L | $AUC_{0-8\,h}$ MTX nmol * h/L | $AUC_{inf}$ MTX nmol * h/L |
|---|---|---|---|
| MTX + vehicle | 277 | 759 | 923 |
| MTX + 20 eq NOV | 363 | 1094 | 1168 |
| Treatment effect of MTX-NOV combination vs. MTX alone | | | |
| Increase (%) | 31 | 44 | 26 |

TABLE 6

Pharmacokinetic parameters of novobiocin following parenteral (i.p.; 5.5 mg/kg) or oral administration (gavage; 55 mg/kg).

| Treatment | $C_{max}$ mg/L | $T_{max}$ (h) | $AUC_{inf}$ mg * h/L |
|---|---|---|---|
| parenteral | 9.6 | 0.9 | 25.5 |
| oral | 23.3 | 1.8 | 109.8 |

Example 8

Pharmacokinetic Study in Healthy Subjects and Rheumatoid Arthritis Patients

Study protocol—In a randomized, double blind, two-arm (N=20 per arm), two-period, cross-over study, healthy volunteers are either treated with 15 mg methotrexate with/without novobiocin (4.5 molar equivalents) via oral administration or treated with 15 mg methotrexate with/without novobiocin (3.0 molar equivalents) via subcutaneous administration. Administrations are separated by a wash-out period of 7-14 days. Blood samples (7.5 mL) are collected in Sarstedt Monovettes® at pre-dose (−30 min) as well as at every 30 min until 3 h after administration, after which samples are collected every 120 min until 12 h after administration, after which samples are collected at t=16, 24 and 48 h, a total of 17 blood samples per dosing and 34 blood samples per subject. Within 30 min after collection, the samples are cooled and centrifuged at 4° C. for 10 min to collect the plasma. Plasma samples are stored at −20° C. until analysis. The primary objective of the study is to evaluate the relative bio-availability of methotrexate following its co-administration with novobiocin. Secondary objectives of the study include the overall tolerability and safety of the co-administration of a therapeutic dose of methotrexate with a non-therapeutic dose of novobiocin for both administration routes overall and in comparison, to administration of methotrexate alone.

Ethics—The study is performed in accordance with the Declaration of Helsinki, and the European GCP, GLP and GMP regulations. The study protocol is reviewed and approved by the appropriate independent ethical committee (IEC) and competent authority. Written informed consent is obtained from all study subjects prior to their enrolment.

Bioanalysis—The plasma levels of methotrexate and novobiocin are determined using LC-MS/MS in MRM (multiple reaction monitoring) mode (see example 7).

Results—Methotrexate and novobiocin are rapidly absorbed both after oral and subcutaneous administration. In general, both routes of administration are well tolerated. The maximum plasma concentrations of both novobiocin and methotrexate are reached faster for the sub cutaneous administration route than for the oral administration route. As expected, sub cutaneous administration of methotrexate alone results in higher maximum concentrations (first pass effect) and total plasma concentrations as compared to oral administration. The plasma levels of methotrexate following the oral co-administration of novobiocin with methotrexate are comparable to the plasma levels of methotrexate following subcutaneous administration of methotrexate alone. The plasma levels of methotrexate following subcutaneous co-administration of novobiocin with methotrexate, significantly exceed the plasma levels of methotrexate following subcutaneous administration of methotrexate alone.

The plasma levels of the topo-isomerase II inhibitor novobiocin remain well below the levels at which any pharmacodynamic effects can be observed in non-clinical models of disease.

Co-administration of methotrexate (15 mg) with 3.0 to 4.5 molar equivalents of novobiocin is safe and well tolerated.

The invention claimed is:

1. An immediate release pharmaceutical composition comprising (i) a therapeutic amount of methotrexate or any pharmaceutically acceptable salts thereof ranging from 5 to 100 mg, (ii) a non-therapeutic amount of novobiocin or any pharmaceutically acceptable salts thereof ranging from 5 to 250 mg, and optionally one or more pharmaceutically acceptable excipients, carriers, or diluents, wherein the ratio of novobiocin to methotrexate in the composition ranges from 0.05 to 20 malar equivalents and the immediate release pharmaceutical composition is in a form suitable for administration to a human subject.

2. The immediate release pharmaceutical composition according to claim 1, comprising 5 to 20 mg of methotrexate and 5 to 40 mg of novobiocin.

3. The immediate release pharmaceutical composition according to claim 1, comprising 5 to 30 mg of methotrexate and 5 to 100 mg of novobiocin.

4. The immediate release pharmaceutical composition according to claim 1, comprising 5 to 45 mg of methotrexate and 5 to 130 mg of novobiocin.

5. The immediate release pharmaceutical composition according to claim 1, comprising 5 to 60 mg of methotrexate and 5 to 150 mg of novobiocin.

6. The immediate release pharmaceutical composition according to claim 1, comprising 5 to 100 mg of methotrexate and 5 to 250 mg of novobiocin.

7. The immediate release pharmaceutical composition according to claim 1, wherein the ratio of novobiocin to methotrexate ranges from 2 to 20 molar equivalents.

8. The immediate release pharmaceutical composition according to claim 1, wherein the ratio of novobiocin to methotrexate ranges from 5 to 20 molar equivalents for oral administration.

9. The immediate release pharmaceutical composition according to claim 1, wherein the ratio of novobiocin to methotrexate ranges from 0.1 to 10 molar equivalents for parenteral administration.

10. The immediate release pharmaceutical composition according to claim 1 comprising two separate compositions, wherein one composition comprises a therapeutic amount of methotrexate or any pharmaceutically acceptable salts thereof and the second composition comprises a non-therapeutic amount of novobiocin or any pharmaceutically acceptable salts thereof, for conjoint treatment.

11. The immediate release pharmaceutical composition according to claim 10, wherein methotrexate is below 20 mg.

12. The immediate release pharmaceutical composition according to claim 10, wherein methotrexate is 15 to 30 mg.

13. The immediate release pharmaceutical composition according to claim 1, wherein the pharmaceutical composition comprises:
    (a) about 1 to about 50 wt % of methotrexate or a pharmaceutically acceptable salt thereof;
    (b) about 0.5 to about 50 wt % of novobiocin or a pharmaceutically acceptable salt thereof;
    a solvent comprising sterile water USP 0 to 98% by weight of the total composition;

(d) an isotonization agent;
(e) an ionization agent; and
(f) optionally other excipients,
wherein weight percentages are percentages of the total weight of the composition.

14. A pharmaceutical product comprising (1) the immediate release pharmaceutical composition according to claim 1, (2) an additional therapeutic agent or a pharmaceutically acceptable salt thereof, and optionally (3) one or more pharmaceutically acceptable excipients, carriers, or diluents.

15. The pharmaceutical product according to claim 14, wherein the additional therapeutic agent is of one or more agents selected from the group consisting of non-steroidal anti-inflammatory agents (NSAIDs), glucocorticosteroids (GCSs), small molecule and/or biologic disease modifying agents (DMARDs), wherein the NSAIDs are selected from the group consisting of meloxicam, celecoxib, rofecoxib, valdecoxib, lumarocoxib, parecoxib and etoricoxib, piroxicam, diclofenac, propionic acids, fenamates, pyrayoleones, and salicylates, wherein the GCSs, are selected from the group consisting of flunisolide, triamcinolone acetonide, betamethasone dipropionate, budesonide, fluticasone propionate, ciclesonide, and mometasone furoate, and wherein the DMARDs are selected from the group consisting of sulfasalazine, leflunomide, hydroxychloroquine, tofacitinib, d-penicillamine, infliximab, adalimumab, etanercept, abatacept, golimumab, anakinra, secukinumab, ixekizumab, rituximab, trastuzumab, certolizumab, tocilizumab, bordalumab, ustekinumab, and belimumab.

16. The immediate release pharmaceutical composition according to claim 13, wherein the isotonization agent is selected from the group consisting of sodium chloride and potassium chloride, the ionization agent is sodium hydroxide, and said other excipients are present and selected from the group consisting of solvents, preservation agents, pH adjusting agents, solubilizers, co-solvents, and combinations thereof.

17. The pharmaceutical product according to claim 15, wherein the additional therapeutic agent is selected from the group consisting of naproxen, flurbiprofen, fenoprofen, ketoprofen, ibuprofen, mefenamic acid, indomethacin, sulindac, ayapropay one, phenylbutazone, and aspirin.

* * * * *